(12) United States Patent
Sim et al.

(10) Patent No.: US 11,578,355 B2
(45) Date of Patent: Feb. 14, 2023

(54) NANOPLASMONIC BIOSENSOR AND METHOD FOR DETECTING DISEASE MARKERS USING THE SAME

(71) Applicant: Korea University Research and Business Foundation, Seoul (KR)

(72) Inventors: Sang Jun Sim, Seoul (KR); Jong-Uk Lee, Seoul (KR); Woo-hyun Kim, Namyangju-si (KR)

(73) Assignee: Korea University Research and Business Foundation, Seoul (KR)

(*) Notice: Subject to any disclaimer, the term of this patent is extended or adjusted under 35 U.S.C. 154(b) by 32 days.

(21) Appl. No.: 16/361,333

(22) Filed: Mar. 22, 2019

(65) Prior Publication Data

US 2019/0360026 A1   Nov. 28, 2019

Related U.S. Application Data

(63) Continuation of application No. PCT/KR2017/010459, filed on Sep. 22, 2017.

(30) Foreign Application Priority Data

Sep. 22, 2016  (KR) .................. 10-2016-0121353
Sep. 22, 2017  (KR) .................. 10-2017-0122344

(51) Int. Cl.
*C12Q 1/6825* (2018.01)
*G01N 21/65* (2006.01)

(52) U.S. Cl.
CPC ......... *C12Q 1/6825* (2013.01); *G01N 21/658* (2013.01)

(58) Field of Classification Search
CPC ............... G01N 21/554; G01N 21/658; G01N 33/553; C12Q 1/6825; C12Q 2565/628; C12Q 2600/178; B82Y 20/00; A61B 2562/0285
See application file for complete search history.

(56) References Cited

U.S. PATENT DOCUMENTS

| | | | |
|---|---|---|---|
| 2007/0050146 A1* | 3/2007 | Bentwich | A61P 35/00 435/6.1 |
| 2008/0076674 A1 | 3/2008 | Litman et al. | |
| 2008/0174775 A1* | 7/2008 | Moskovits | G01N 21/658 356/301 |
| 2011/0053794 A1* | 3/2011 | Zhang | B01J 19/0046 506/9 |
| 2011/0166045 A1 | 7/2011 | Dhawan et al. | |
| 2014/0176942 A1* | 6/2014 | Bratkovski | G01N 21/01 356/301 |
| 2015/0126393 A1* | 5/2015 | Corn | C09D 5/006 506/16 |
| 2015/0223739 A1* | 8/2015 | Walavalkar | A61B 5/0075 600/342 |
| 2015/0253317 A1 | 9/2015 | Singamaneni et al. | |
| 2015/0253318 A1* | 9/2015 | Singamaneni | B82Y 20/00 435/6.19 |
| 2015/0338346 A1 | 11/2015 | Chou et al. | |

FOREIGN PATENT DOCUMENTS

| | | |
|---|---|---|
| CN | 102175664 A | 9/2011 |
| CN | 102661941 A | 9/2012 |
| CN | 104380084 A | 2/2015 |
| CN | 104823049 A | 8/2015 |
| CN | 105823768 A | 8/2016 |
| WO | WO-2014134144 A1 * | 9/2014 ............. A61K 49/10 |

OTHER PUBLICATIONS

Ding et al "Surface plasmon resonance biosensor for higly sensitive detection of microRNA base on DNA super-sandwich assemblies and streptavidin signal amplification" Analytica Chimica Acta, 2015 874: 59-65. (Year: 2015).*
Kang et al "Ultra-specific zeptomole micorRNA detection by plasmonic nanowire interstice sensor with bi-temperature hybridization" Small, 2014, 10(20): 4200-4206. (Year: 2014).*
Jansen, Henri, et al. "The black silicon method: a universal method for determining the parameter setting of a fluorine-based reactive ion etcher in deep silicon trench etching with profile control", *Journal of Micromechanics and Microengineering*, vol. 5, No. 2, 1995, (pp. 115-120).
Válóczi, Anna, et al. "Sensitive and specific detection of microRNAs by northern blot analysis using LNA-modified oligonucleotide probes", *Nucleic acids research*, vol. 32, No. 22, Dec. 14, 2004 (pp. 1-7).
Chen, Caifu, et al. "Real-time quantification of microRNAs by stem-loop RT-PCR", *Nucleic acids research*, vol. 33, No. 20, Feb. 2005, (pp. 1-9).
Ma, Li, et al., "Tumour invasion and metastasis initiated by microRNA-10b in breast cancer", *Nature*, vol. 449, Oct. 11, 2007 (pp. 682-690).
Huang, Qihong, et al., "The microRNAs miR-373 and miR-520c promote tumour invasion and metastasis", *Nature cell biology* 10.2, 2008 (pp. 202-226).
Yan, Li-Xu et al. "MicroRNA miR-21 overexpression in human breast cancer is associated with advanced clinical stage, lymph node metastasis and patient poor prognosis", RNA, vol. 14, Issue 11, 2008 (pp. 2348-2360).
Porter, Marc D., et al., "SERS as a bioassay platform: fundamentals, design, and applications", *Chemical Society Reviews*, Issue 5, 2008 (pp. 1001-1011).
Diebold, Eric D., et al. "Femtosecond Laser-Nanostructured Substrates for Surface-Enhanced Raman Scattering", *Langmuir*, 25.3, Jan. 9, 2009 (pp. 1790-1794).

(Continued)

*Primary Examiner* — Katherine D Salmon
(74) *Attorney, Agent, or Firm* — NSIP Law

(57) ABSTRACT

The present invention relates to a nanoplasmonic biosensor capable of label-free multiplex detection of disease markers in blood with high selectivity and sensitivity and a method for detecting disease markers using the nanoplasmonic biosensor. The nanoplasmonic biosensor of the present invention enables label-free multiplex detection of miRNAs as disease markers in blood with high selectivity and sensitivity. Therefore, the nanoplasmonic biosensor of the present invention can be effectively used for the diagnosis of miRNA-related diseases and clinical applications.

6 Claims, 18 Drawing Sheets

Specification includes a Sequence Listing.

(56) References Cited

OTHER PUBLICATIONS

Chang, Allan SP, et al. "Nanopillars array for surface enhanced Raman scattering." *Advanced Environmental, Chemical, and Biological Sensing Technologies VIII*. International Society for Optics and Photonics, vol. 8024, Apr. 20, 2011 (11 pages in English).
Cortez, Maria Angelica, et al., "MicroRNAs in body fluids—the mix of hormones and biomarkers", *Nature reviews Clinical oncology*, vol. 8, Issue 8, 2011, (pp. 467-477).
Sharma, Bhavya, et al. "SERS: Materials, applications, and the future", *Materials today*, Issue 15 Issues 1-2, Jan.-Feb. 2012 (pp. 16-25).
Zhang, Zhong Ju, et al., "miRNAs in breast cancer tumorigenesis", Oncology *reports*, vol. 27, Issue Apr. 4, 2012 (pp. 903-910).
Abell, Justin L., et al. "Label-Free Detection of Micro-RNA Hybridization Using Surface-Enhanced Raman Spectroscopy and Least-Squares Analysis", *Journal of the American Chemical Society*, 134.31 Jul. 19, 2012, (pp. 12889-12892).
Schmidt, Michael et al., "Large Area Fabrication of Leaning Silicon Nanopillars for Surface Enhanced Raman Spectroscopy", *Advanced Materials*, vol. 24, 2012, (pp. OP11-OP18).
Hamidi-Asl, Ezat, et al. "A review on the electrochemical biosensors for determination of microRNAs", *Talanta*, Issue 115, Oct. 15, 2013 (pp. 74-83).
Gracie, Kirsten, et al., "Simultaneous detection and quantification of three bacterial meningitis pathogens by SERS", *Chemical Science*, Issue 3, 2014, (pp. 1030-1040).
Johnson, Blake N., et al., "Biosensor-based microRNA detection: techniques, design, performance, and challenges", *Analyst*, Issue 7,2014 (pp. 1576-1588).
Wong, Chi Lok, et al., "Non-labeling multiplex surface enhanced Raman scattering (SERS) detection of volatile organic compounds (VOCs)", *Analytica chimica acta*, vol. 844, Sep. 24, 2014 (pp. 54-60).
Joshi, Gayatri K., et al. "Highly specific plasmonic biosensors for ultrasensitive microRNA detection in plasma from pancreatic cancer patients", *Nano letters*, Issue 14, No. 12 Nov. 7, 2014 (pp. 6955-6963).
Tian, Tian, et al., "A review: microRNA detection methods", *Organic & biomolecular chemistry*, Issue 8, 2015 (pp. 2226-2238).
Nguyen, Anh H., et al., "Plasmonic coupling-dependent SERS of gold nanoparticles anchored on methylated DNA and detection of global DNA methylation in SERS-based platforms", *Journal of Optics*, vol. 17, Issue 11, Oct. 23, 2015 (pp. 1-12).
Lee, Jong Uk et al., "A nanoplasmonic biosensor for label-free multiplex detection of cancer biomarkers", *Biosensors and Bioelectronics*, Issue 74, Dec. 15, 2015 (pp. 341-346).
Larrea, Erika, et al., "New Concepts in Cancer Biomarkers: Circulating miRNAs in Liquid Biopsies", *International journal of molecular sciences*, vol. 17, Issue 5 Apr. 2016 (pp. 1-42).
Frøhling, Kasper Bayer, et al., "Surface-enhanced Raman spectroscopic study of DNA and 6-mercapto-1-hexanol interactions using large area mapping", *Vibrational Spectroscopy*, vol. 86, Sep. 2016 (pp. 331-336).
International Search Report dated Jan. 19, 2018 in corresponding International Patent Application No. PCT/KR2017/010459 (3 pages in English and 3 pages in Korean).
Korean Office Action dated Jan. 21, 2019 in corresponding Korean Patent Application No. 10-2017-0122344 (4 pages in English and 5 pages in Korean).
Hu, Min, et al., "Gold Nanofingers for Molecule Trapping and Detection," *Journal of the American Chemical Society*, 132, 37, 2010 (pp. 12820-12822).
Kang, Taejoon, et al., "Ultra-Specific Zeptomole MicroRNA Detection by Plasmonic Nanowire Interstice Sensor with Bi-Temperature Hybridization." *Small*, 10, 20, 2014 (pp. 4200-4206).
Chinese Office Action dated Sep. 29, 2021 in counterpart Chinese Patent Application No. 201780071875.2 (5 pages in Chinese).

* cited by examiner

I: miR-10b probe
II: miR-21 probe
III: miR-373 probe

A: Target miR-10b
B: Target miR-21
C: Target miR-373

A)

B)

A)

B)

A)

B)

NANOPLASMONIC BIOSENSOR AND METHOD FOR DETECTING DISEASE MARKERS USING THE SAME

CROSS-REFERENCE TO RELATED APPLICATIONS

This application is a continuation of International Application No. PCT/KR2017/010459 filed on Sep. 22, 2017, which claims the benefit of Korean Patent Application No. 10-2016-0121353 filed on Sep. 22, 2016, and Korean Patent Application No. 10-2017-0122344 filed on Sep. 22, 2017 in the Korean Intellectual Property Office, the entire disclosures of which are incorporated herein by reference for all purposes.

TECHNICAL FIELD

The present invention relates to a nanoplasmonic biosensor capable of label-free multiplex detection of disease markers in blood with high selectivity and sensitivity and a method for detecting disease markers using the nanoplasmonic biosensor.

BACKGROUND ART

Cancer, one of the most life-threatening diseases, represents the leading cause of morbidity and mortality, with approximately 14 million new cases and 8.2 million cancer-related deaths in 2012, and this number is predicted to rise by approximately 70% over the next two decades (Larrea E., Sole C., Manterola L., Goicoechea I., Armesto M., Arestin M., Caffarel M. M., Araujo A. M., Araiz M., Fernandez-Mercado M. and Lawrie C. H., Int. J. 2016, Mol. Sci. 17, 627). Accordingly, the need for advanced and effective cancer diagnosis is increasing. According to the above statistics, the detection of cancer in the early and metastatic stages is an essential prerequisite for the effective diagnosis and treatment of cancer. However, it is difficult to collect sufficiently large amounts of sample at the early stages of cancer and conventional biomarkers are often only observed at the disease's onset. Thus, studies have been conducted to investigate bio-informative and suitable biomarkers for more effective diagnoses.

In this process, miRNAs have attracted new attention as pivotal regulators of intracellular gene expression. miRNAs complementarily bind to target mRNAs during transcription. miRNAs indicate the initial phase of cancer and the tumour stage's progression in tissue and blood through different expression levels (Zhang Z. J. and MA S. L., 2012. ONCOLOGY REPORTS 27, 903-910). In particular, recent studies have shown that miRNAs can be released from cells and secreted in human biofluids, including blood serum, plasma, urine and saliva (Cortez M. A., Bueso-Ramos C., Ferdin J., Lopez-Berestein G., Sood A. K., and Calin G. A., 2011, Nature Reviews Clinical Oncology, 8, 467-477). This release can occur both in response to the apoptosis and necrosis of cancer cells and as an active release; furthermore, miRNAs contain specific cancer information and have high stability in both plasma and serum. Due to their advantages, these miRNAs, called circulating cell-free miRNAs, can act as noteworthy biomarkers in cancer diagnoses. miR-10b, overexpressed in metastatic cancer cells, is induced by the transcription factor Twist directly binding to the promoter of miR-10b (MIRN10B) and regulates the translation of messenger RNA encoding homeobox D10, resulting in an increase in the expression of the well-known pro-metastatic gene RHOC (Ma L., Teruya-Feldstein J. and Weinberg R. A., 2007. NATURE 449). Some studies have demonstrated that several miRNAs are upregulated in the metastatic state of some cancers including glioblastoma, breast cancer, lung cancer and chronic lymphocytic leukaemia than in normal cells (Yan L. X., Huang X. F., Shao Q., Huang Y. M., Deng L., Wu Q. L., Zeng Y. X. and Shao J. Y., 2008. RNA 14, 2348-2360). miR-21 is the most abundantly expressed upregulated miRNA that regulates the RAS p21 protein activator 1 (RASA1) gene. The overexpression of miR-373 induces the migration of cancer cells, suppresses the oncogene-induced p53 pathway through direct inhibition of the LATS2 cancer tumor, and partially promotes cellular transformation of oncogenic RAS. Further, miR-373 is inversely correlated with the CD44 surface glycoprotein expression and is upregulated in the clinical stage of cancer metastasis (Huang Q., Gumireddy K., Schrier M., Le Sage C., Nagel R., Nair S. Egan D. A., Li A., Huang, G. H., Klein-Szanto A. J., Gimotty P. A., Katsaros D., Coukos G., Zhang L., Pure E. and Agami R., 2008 Nature Cell Biology 10.2, 202-10). These studies reveal that miRNAs can be used as important biomarkers for cancer diagnosis and prognosis. Hence, an advanced detection system that identifies the miRNA expression level in a blood sample is being investigated.

miRNA detection systems have been developed by various methods over the past years. Northern blotting and cloning are traditional standard methods for miRNA detection (Valoczi A., Hornyik C., Varga N., Burgyan J., Kauppinen S. and Havelda Z., 2004. Nucleic Acids Res. 32(22), e175). In recent years, RT-PCR and microarrays are most widely used to detect miRNAs. However, RT-PCR and microarrays require cDNA synthesis, expensive reagents, and fluorescent materials (Chen C., Ridzon D. A., Broomer A. J., Zhou Z., Lee D. H., Nguyen J. T., Barbisin M., Xu N. L., Mahuvakar V. R., Andersen M. R., Lao K. Q., Livak K. J. and Guegler K. J., 2005. Nucleic Acids Res. 33(20), e179). Such miRNA detection methods are limited in that miRNAs are composed of small nucleotides and are present in small quantities in blood and they are focused on qualitative analysis only (Hamidi-Asl E., Palchetti I., Hasheminejad E., and Mascini M., 2013. Talanta 115, 74-83). Thus, miRNA in-situ detection methods and quantitative real-time PCR (qRT-PCR) techniques have been reported recently. However, these methods and techniques involve pre-processing steps and require additional labeling for target miRNA detection and quantification. This labeling causes chemical modification of DNA, incurring considerable costs and making the miRNA detection more complex (Abell J. L., Garren J. M., Driskell J. D., Tripp R. A., and Zhao Y., 2012. J. Am. Chem. Soc 134, 12889-12892). Fluorescence-based methods are sensitive to quenching effects from the excitation light or environmental factors. This drawback is considered as a major obstacle to the application of fluorescence-based methods to actual patient diagnosis.

In attempts to solve the above problems, novel improved methods for miRNA detection with high sensitivity and selectivity were reported. Of these, PCR-free signal amplification techniques, including primer extension, isothermal index amplification, and rolling cycle amplification, can offer solutions to the problems caused by inefficient and inaccurate amplification. Second, electrical methods such as SPR based on nanomaterials, including gold nanoparticles, quantum dots, and magnetic particles are known (Tian T., Wang J. and Zhou X., 2015 Org. Biomol. Chem. 13, 2226-2238). Particularly, surface-enhanced Raman scattering (SERS) is an improved method for miRNA detection and its sensitivity is known to be higher by a factor of $10^4$ to $10^9$ than those of previous Raman scattering measurements (Nguyen A. H., Lee J. U. and Sim S. J., 2015. J. Opt. 17, 114022). Improved Raman signals on metal surfaces are attributed to localized surface plasmon resonances (LSPRs) between the metal and analytes caused by the vibration of electrons around the molecules (Lee J. U., Nguyen A. H., and Sim S. J., 2015. Biosensors and Bioelectronics 74 341-346). For metals, plasmon resonance scattering of nanoscale structure surfaces is dependent on the robustness of the structural conformation that significantly improves the reproducibility and electromagnetic (EM) field (Sharma B., Frontiera R. R., Henry A. I., Ringe E., and Van Duyne R. P., 2012. Materialstoday 15 1-2). However, traditional problems (such as low signal reproducibility) of SERS are continuously addressed.

DETAILED DESCRIPTION OF THE INVENTION

Problems to be Solved by the Invention

The present invention has been made in an effort to solve the above-described problems and intends to provide a label-free, multiplex nanoplasmonic biosensor for the detection of miRNAs as disease markers with high selectivity and sensitivity and a method for detecting disease markers using the nanoplasmonic biosensor.

Means for Solving the Problems

One aspect of the present invention provides a nanoplasmonic biosensor including: a substrate having a plurality of protrusions spaced apart from one another on one surface thereof; a plurality of gold nanopillars formed by coating gold particles on the protrusions and in the form of thin films surrounding the protrusions; and a capture part conjugated with the end of at least one of the gold nanopillars, wherein the capture part is a first single-stranded DNA or LNA including a sequence complementary to a portion of the sequence of a miRNA as a disease marker.

According to the present invention, when the miRNA binds to the capture part, the ends of at least two of the gold nanopillars may be converged towards a specific location.

When the miRNA binds to the capture part, the Raman signal may be primarily amplified.

According to the present invention, the nanoplasmonic biosensor may further include a detection part as a second single-stranded DNA or LNA including a sequence complementary to another portion of the sequence of the miRNA.

When the miRNA binds to the detection part, the Raman signal may be secondarily amplified.

According to the present invention, the thiol group at one end of the first single-stranded DNA or LNA may be modified.

According to the present invention, the substrate may be made of Si and the protrusions may extend from the one surface of the substrate.

According to the present invention, the one surface of the substrate may be covered with the gold particles.

According to the present invention, the miRNA may be selected from the group consisting of miR-10b, miR-21, miR-373, miR-222, and miR-200C.

A further aspect of the present invention provides a method for detecting disease markers using the nanoplasmonic biosensor.

Effects of the Invention

The nanoplasmonic biosensor of the present invention enables label-free multiplex detection of miRNAs as disease markers in blood with high selectivity and sensitivity. Therefore, the nanoplasmonic biosensor of the present invention can be effectively used for the diagnosis of miRNA-related diseases and clinical applications.

BEST MODE FOR CARRYING OUT THE INVENTION

The present invention will now be described in more detail.

The present invention is directed to a nanoplasmonic biosensor capable of label-free multiplex detection of miRNAs as disease markers in blood with high selectivity and sensitivity and a method for detecting disease markers using the nanoplasmonic biosensor.

Figure 1:
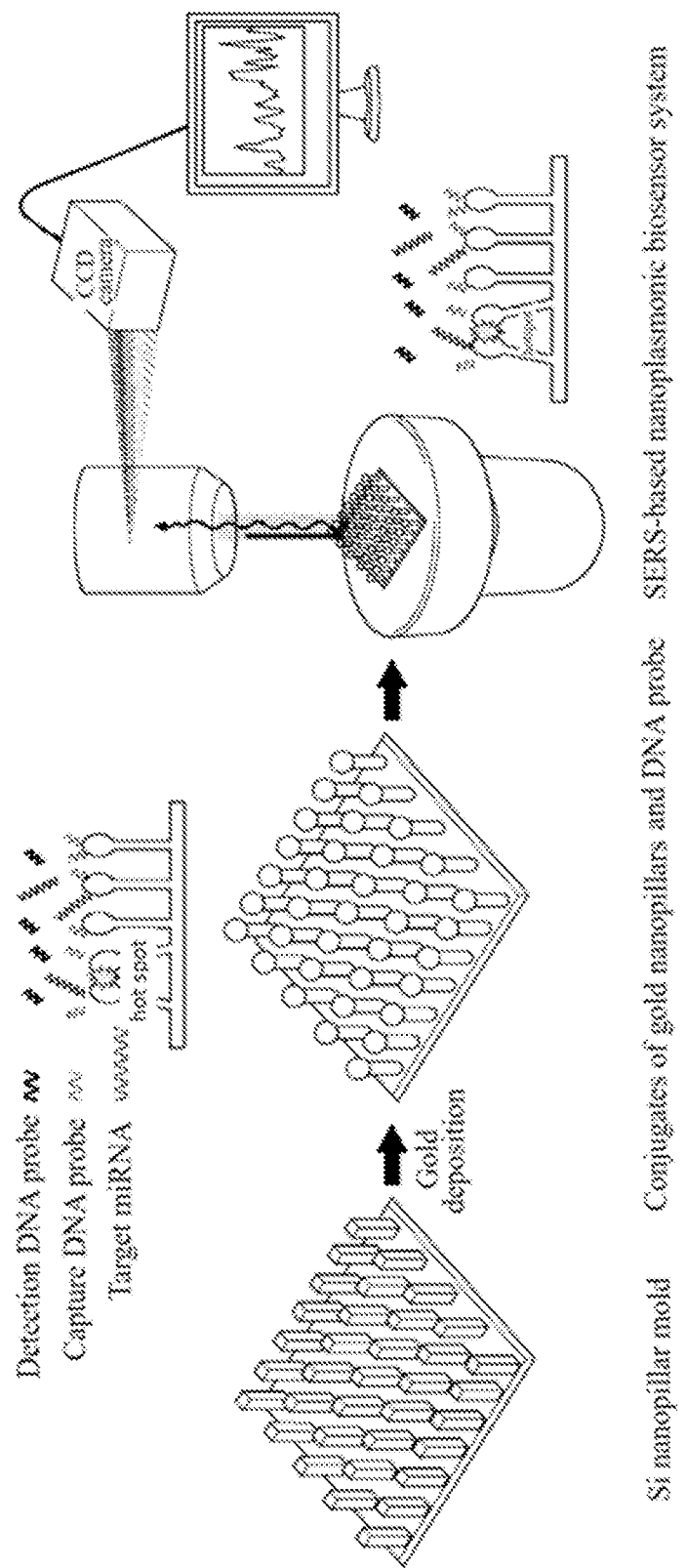
FIG. 1 is a schematic conceptual diagram showing the fabrication of a nanoplasmonic biosensor according to the present invention and the detection of a disease marker using the nanoplasmonic biosensor.

FIG. 1 is a schematic conceptual diagram showing the fabrication of a nanoplasmonic biosensor according to the present invention and the detection of a disease marker using the nanoplasmonic biosensor. As shown in FIG. 1, the nanoplasmonic biosensor of the present invention uses a primarily amplified Raman signal based on the phenomenon that when a first single-stranded DNA (capture DNA) or locked nucleic acid (LNA) conjugated with the ends of gold nanopillars and including a sequence complementary to a portion of the sequence of a miRNA as a disease marker is hybridized with the miRNA, the ends of at least two of the gold nanopillars are converged towards a specific location (hereinafter, also referred to as "head-flocked") and a secondarily amplified Raman signal through complete hybridization of a second single-stranded DNA (detection DNA) or LNA including a sequence complementary to another portion of the sequence of the miRNA with the miRNA after hybridization with the first single-stranded DNA or LNA, enabling label-free multiplex detection of the disease marker in blood with high selectivity and sensitivity.

Specifically, the nanoplasmonic biosensor of the present invention includes: a substrate having a plurality of protrusions spaced apart from one another on one surface thereof; a plurality of gold nanopillars formed by coating gold particles on the protrusions and in the form of thin films surrounding the protrusions; and a capture part conjugated with the end of at least one of the gold nanopillars. The capture part is a first single-stranded DNA or LNA including a sequence complementary to a portion of the sequence of a miRNA as a disease marker.

When the miRNA binds to the capture part, the ends of at least two of the gold nanopillars may be converged towards a specific location (head-flocked), and as a result, the Raman signal may be primarily amplified.

The nanoplasmonic biosensor of the present invention may further include a detection part as a second single-stranded DNA or LNA including a sequence complementary to another portion of the sequence of the miRNA. The presence of the detection part enables label-free multiplex detection of the disease marker with high selectivity and sensitivity.

When the miRNA binds to the detection part, complete hybridization of the miRNA, the first DNA (or LNA), and the second DNA (or LNA) is achieved, resulting in secondary amplification of the Raman signal. Based on the Raman signal obtained through complete hybridization of the miRNA, the first DNA (or LNA), and the second DNA (or LNA), fingerprint peaks of the target miRNA can be identified while determining whether hybridization occurs by nonspecific binding, enabling label-free multiplex detection of the disease marker with high selectivity and sensitivity.

The thiol group at one end of the first single-stranded DNA or LNA is modified, which is preferable for efficient conjugation with the gold nanopillars.

Preferably, the substrate is made of Si and the protrusions extend from the one surface of the substrate.

The one surface of the substrate is preferably covered with the gold particles.

The miRNA may be any of those that can be used as disease markers. For example, the miRNA may be selected from the group consisting of miR-10b, miR-21, miR-373, miR-222, and miR-200C.

The present invention also provides a method for detecting miRNAs as disease markers in blood using the nanoplasmonic biosensor.

MODE FOR CARRYING OUT THE INVENTION

The present invention will be described in more detail with reference to the following examples. It will be obvious to those skilled in the art that these examples are provided for illustrative purposes and the scope of the invention is not limited thereto.

Materials and Methods

Materials

BOROFLOAT® 33 was purchased from Schott Korea (Korea). Au pellet (ϕ 3×3 h, 99.99%) was purchased from Sin-woo Metal (Korea). Human serum, sodium sulfate anhydrous ($Na_2SO_4$), sodium chloride ($NaCl_2$), trisodium citrate, hydrochloric acid (HCl, 37 wt % in water), 6-mercapto-1-hexanol (MCH, 97%), 1,4-dithiothreitol (DTT), and ethyl acetate (anhydrous 99.8%) were purchased from Sigma Aldrich (Korea). Ambion® nuclease-free water was purchased from Thermo Fisher Scientific (Korea). DNA LoBind (1.5 mL) tubes were purchased from Eppendorf. Ultra-pure water (18.2 mΩ $cm^{-1}$) was used to prepare all solutions. All DNA probes, target miRNAs, and single-base mismatched miRNAs were purchased from Bioneer (Korea). Thiolated and Cy3-tagged LNA probes were purchased from Eurogentec (Seraing, Belgium) and an Exosome RNA Isolation Kit was purchased from Thermo Fisher Scientific (Waltham, Mass., USA).

Synthesis of the DNA Probe (or LNA) for Hybridization with Target miRNAs miRNAs were synthesized and their complementary sequences were taken from the miRbase site. DNA (or LNA) probes were designed with two different parts, including a first DNA (or LNA) (capture DNA (or LNA)) and a second DNA (or LNA) (detection DNA (or LNA)). To confirm the SERS signal transition with each step of hybridization between the DNA probe and the target miRNA, the roles of the DNA probe were separated. The first DNA (capture part) plays the role of a conjugation DNA probe with the head-flocked gold nanopillar structure. The second DNA (detection part) acts to identify complete hybridization. To hinder the nonspecific binding between the second DNAs and target miRNAs for multiplex detection, the G-C content ratio (40-60%) and melting points ($T_m$) were considered when the sequence of each second DNA was determined and the sequences of the second DNAs were designed such that three consecutive bases do not overlap when sequences complementary to the sequences of the miRNAs were determined with the first DNAs and the second DNAs. miR-10b, miR-21, and miR-373 were used as the miRNAs. Using the OligoAnalyzer Tool from Integrated DNA Technologies (IDT), the G-C content ratio, $T_m$ values, length, self-dimer and heterodimer of each probe were confirmed (Tables 1 and 3). For efficient conjugation of the first DNA capture part with gold nanopillars, the thiol group at the 5'-end of the first DNA from Bioneer (Korea) was modified.

The miRNAs used in the present invention employed the sequences shown in Table 2 based on the miRNA database from the miRbase. The thiol groups (—SH) at the 5'-ends of the first and second DNAs and the first and second LNAs were modified with materials that can activate thiol groups. In Tables 2 and 3, each plus sign (+) indicates that the following base is an LNA base.

TABLE 1

| Probe | Length (nt) | C-G contents (%) | $T_m$ (° C.) |
|---|---|---|---|
| miR-10b capture | 12 | 41.7 | 31.8 |
| miR-10b detection | 11 | 45.5 | 30.8 |
| miR-21 capture | 11 | 36.4 | 24.3 |
| miR-21 detection | 11 | 36.4 | 29.1 |
| miR-373 capture | 12 | 50 | 37.5 |
| miR-373 detection | 11 | 45.5 | 34.2 |

TABLE 2

| Type | miRNA | (SEQ ID NO:) | (SEQ ID NO:) | (SEQ ID NO:) |
|---|---|---|---|---|
| DNA | miR-10b | (SEQ ID NO: 1) | (SEQ ID NO: 5)5'-thiol modified | (SEQ ID NO: 9) |
| DNA probe | miR-21 | (SEQ ID NO: 2) | (SEQ ID NO: 6)5'-thiol modified | (SEQ ID NO: 10) |
| DNA probe | miR-373 | (SEQ ID NO: 3) | (SEQ ID NO: 7)5'-thiol modified | (SEQ ID NO: 11) |
| LNA | miR-10b | (SEQ ID NO: 4) | (SEQ ID NO: 8)5'ThioMC6-D modified | (SEQ ID NO: 12) |

TABLE 3

| | Designation | (SEQ ID NO:) | Length (bp) | Tm (° C.) |
|---|---|---|---|---|
| miRNA | miR-21 | (SEO ID NO: 13) | 22 | |
| | miR-21 A | (SEQ ID NO: 14) | 22 | |
| | miR-21 B | (SEQ ID NG: 15) | 22 | |
| | miR-222 | (SEQ ID NO: 16) | 21 | |
| | miR-222 A | (SEQ ID NO: 17) | 21 | |
| | miR-222 B | (SEQ ID NG: 18) | 21 | |
| | miR-200c | (SEQ ID NO: 19) | 23 | |
| | miR-200c A | (SEQ ID NO: 20) | 23 | |
| | miR-200c B | (SEQ ID NO: 21) | 23 | |
| | miR-200a | (SEQ ID NO: 22) | 22 | |
| | miR-200b | (SEQ ID NG: 23) | 22 | |
| LNA capture probe | miR-21 | (SEQ ID NO: 24)5' Thiol/C6 modified | 12 | 70 |
| | miR-222 | (SEQ ID NO: 25)5' Thiol/C6 modified | 11 | 72 |
| | miR-200c | (SEQ ID NO: 26)5' Thiol/C6 modified | 12 | 71 |
| LNA detection probe | miR-21 | (SEQ ID NO: 27)5' Cy3 modified | 10 | 70 |
| | miR-222 | (SEQ ID NO: 28)5' Cy3 modified | 10 | 73 |
| | miR-200c | (SEQ ID NO: 29)5' Cy3 modified | 11 | 73 |

Fabrication of the Head-Flocked Gold Nanopillar Structure

For head-flocked gold nanopillar fabrication, an elastic silicon nanopillar mold was fabricated using a maskless reactive ion plasma etching (RIE) process (Wong C. L., Dinish U. S., Schmidt M. S., and Olivo M., 2014. Analytica Chimica Acta 844, 54-60). The maskless RIE process is a dry etching method that uses chemically reactive plasma without a film mask to generate the nanopillar shape (Schmidt M. S., Hubner J., and Boisen A., 2012. Adv. Mater. 24, 11-18).

Four-inch p-type silicon wafers were used, and etching was performed using a Plasma Lab100 instrument from Oxford Instruments (Micro/Nano Fab Center, Korea Institute of Science and Technology) with the following parameters: $SF_6$: $O_2$ flow ratio (1.12), platen power (110 W), chamber pressure (36 mTorr) and rate (3 nm/s). To avoid effects on the subsequent SERS spectrum, the maskless reactive ion etching process was followed by the physical removal of remnants by exposure to oxygen plasma. To metalize the elastic silicon nanopillar mold, gold was coated on the elastic silicon nanopillar through an electron beam evaporation process. In this process, the metallization deposited more gold on the head of the elastic silicon nanopillar structure. Head-flocking was observed during liquid sample treatment and was confirmed by scanning electron microscopy (SEM). Additionally, cast slide glass was fabricated using silicate glass (BOROFLOAT® 33). Since this cast was designed by the AutoCAD program and the number and size of the cast could be controlled, it became the basis of the multiplex system. Each head-flocked gold nanopillar substrate was loaded on the cast slide glass to detect the target miRNAs.

Fabrication of Nanoplasmonic Biosensor and Hybridization of the First DNA (or LNA), the Second DNA (or LNA) and Target miRNA For the fabrication of a nanoplasmonic biosensor according to the present invention, the thiol group in the first DNA (capture DNA) was activated using dithiothreitol (DTT), which is a reducing agent, with the formation of a disulfide bond by the 2 serial thiol-disulfide interchange reaction. Since the first DNA (capture DNA) had a disulfide bond at the 5'-end, DTT that could break the disulfide bond was used. A solution of the first probe (1 μM) was added to a conjugation buffer containing $Na_2SO_4$ (30 mM) and nuclease-free water (pH~7).

Next, the gold nanopillar substrate was incubated in the first DNA probe solution for 12 h at 30° C. After incubation, the gold nanopillar substrate was washed with deionized (DI) water and flushed with $N_2$. Self-assembled monolayers consisting of 6-mercapto-1-hexanol (MCH) play an important role as spacers that prevent the nonspecific binding that occurs when DNA strands bind to gold or silver surfaces (Frøhling K. B., Alstrøm T. S., Bache M., Schmidt M. S., Schmidt M. N., Larsen J., Jakobsen M. H., and Boisen A., 2016. Vibrational Spectroscopy 86, 331-336). MCH (10 μM) solution was added to the conjugation buffer. The gold nanopillar substrate was incubated in MCH solution for 3 h at room temperature and was then washed by using washing buffer, including 2×SSC and 0.2% SDS.

After the previous step, the substrate was completely washed with DI water and flushed with $N_2$. For hybridization between the first DNA and the target miRNA, human serum was spiked with synthesized target miRNAs ranging from 100 aM to 1 μM. The gold nanopillar substrate conjugated with the first DNA was incubated for 12 h at 30° C., followed by washing out unhybridized target miRNAs with DI water and $N_2$ drying. To hybridize the second DNA (detection DNA) probe with miRNA, hybridization buffer consisting of 2×SSC, nuclease-free water, and the second DNA probe (1 μM) was prepared at 30° C. for 12 h, followed by washing out with DI water and $N_2$ drying.

(2) The nanoplasmonic biosensor of the present invention was fabricated by the following procedure. First, the thiol group of the first LNA (capture LNA) probe was activated with dithiothreitol (DTT). The capture LNA (1 μM) was incubated with the SERS substrate in 3×SSC/0.04 SDS for 12 h, washed twice with 2×SSC/0.1 SDS at 30° C. to remove excess LNA, followed by $N_2$ drying. To hinder the nonspecific binding, the SERS substrate treated with the capture LNA was incubated in MCH (10 μM) for 3 h and washed twice with washing buffer. The SERS substrate was incubated with exosomal miRNAs in 5×SSC in a hybridization incubator (FINEPCR, Gyeonggi-do, Korea) at 42° C., rinsed with washing buffer preheated to 42° C. to remove unhybridized exosomal miRNAs, washed with water treated with diethyl pyrocarbonate (DEPC), followed by $N_2$ drying. Then, the substrate was immersed in a solution containing the second LNA (detection LNA, 1 μM) probe, 5×SSC, 0.1% SDS, and DEPC-treated water at 64° C. for 4 h, cleaned with 0.1% SDS-containing 2×SSC and DEPC-treated water, followed by $N_2$ drying.

Cell Culture

AU565, BT474, HCC1143, MCF-7, MCF-10A, MDA-MB-231 and SKBR3 cell lines were purchased from American Type Culture Collection (Manassas, Va., USA). AU565, HCC1143, MDA-MB-231 and SKBR3 cells were cultured in Roswell Park Memorial Institute (RPMI)-1640 media (Hyclone, Logan, Utah, USA), BT474 cells were cultured in Dulbecco's modified Eagle medium (DMEM, Welgene, Seoul, Korea), MCF-10A cells were cultured in DMEM/F12 1:1 (Hyclone), MCF-7 cells were cultured in RPMI 1640 medium supplemented with human recombinant insulin (4 mg $mL^{-1}$, zinc solution; Life Technologies, Grand Island, N.Y., USA). Culture media for AU565, BT474, HCC1143, MCF-7, MDA-MB-231 and SKBR3 cells were supplemented with 10% fetal bovine serum, 100 U $mL^{-1}$ penicillin, 100 mg $mL^{-1}$ streptomycin, and 2 mM L-glutamine A culture medium for MCF-10A cells was supplemented with 2.5 mM L-glutamine, 15 mM HEPES, 20 ng $mL^{-1}$ human epidermal growth factor, 0.01 mg $mL^{-1}$ bovine insulin, 500 ng $mL^{-1}$ hydrocortisone, and 5% horse serum. All cells were kept at 37° C. and 5% $CO_2$.

Isolation of Exosomes from Cancer Cell Lines and Purification of Exosomal miRNAs After cells were cultured for 24 h, the culture supernatant (150 mL) was collected and centrifuged at 300×g for 10 min at 4° C. to remove dead cells and debris. Next, cell debris and microvesicles were further removed at 2,000×g for 10 min at 4° C. and at 10,000×g for 30 min at 4° C. The supernatant was collected, concentrated to a final volume of 500 μL using Amicon Ultra-15 centrifugal filter unit with a 10-kDa membrane (Merck Millipore, Billerica, Mass., USA) and loaded onto a qEV size-exclusion column (Izon Science Ltd., Christchurch, New Zealand).

The supernatant was eluted in 0.5-mL fractions with PBS; Fractions 7-11 were highly concentrated for exosomes. The eluate from the qEV column was concentrated to a final volume of ~200 μL using Amicon Ultra-0.5 centrifugal filter unit (Merck Millipore) and exosomal miRNAs were purified using a Total Exosome RNA and Protein Isolation Kit (Invitrogen, Carlsbad, Calif., USA) before analysis. The final purified solution containing exosomal miRNAs (10 μL) was diluted to 200 μL with 5×SSC.

qRT-PCR

The content of exosomal miRNAs in each cell line was quantified by qRT-PCR. The total RNA (1 to 10 ng per 15 μL-reaction) was reversely transcribed using a TaqMan miRNA reverse transcription kit (Applied Biosystems) at 16° C. for 30 min, at 42° C. for 30 min, and at 85° C. for 5 min.

Real-time qPCR was performed using a TaqMan miRNA analysis kit (Applied Biosystems, Foster City, Calif., USA) and a TaqMan universal PCR master mix II (2×; Applied Biosystems) with an Applied Biosystems StepOnePlus real-time PCR system (Applied Biosystems, Inc.) at 95° C. for 10 min, at 95° C. for 15 sec, and at 60° C. for 1 min. This thermal cycling was repeated 40 times. Cycle threshold (Ct) values were calculated using the SDS software (v2.0.1, Applied Biosystems). Data were normalized relative to an endogenous control (miR-1659) using the 2-ΔΔCt method and then the relative expression levels of exosomal miRNAs were determined.

Detection of miRNA and Relative Quantitative Analysis Based on SERS

After conjugation of the gold nanopillar substrate with the first DNA and sampling of miRNAs and the second DNA, these gold nanopillar chips were loaded into cast slide glass for the multiplex measurement. Using silicone gel, the head-flocked gold nanopillar chips were attached to the cast slide glass loading areas. The SERS signals of the DNA probe and miRNA were measured using Raman microscopy from NOST (Korea). The excitation laser (785 nm) was focused through the 100× air objective (TU Plan ELWD 100×, Nikon, 0.6 NA, 0.56 mm WD) of an upright microscope (Eclipse Ni-U, Nikon). The direction of light polarization was controlled by using a linear polarizer (PRM 1/M, Thorlabs). The intensity of the laser was set at 10.67 mW using a digital power meter (PM100, Thorlabs). To obtain the optimal condition for the SERS measurement, various experimental conditions of exposure time, confocal slit, accumulation number, and ND filter ratio were used. The exposure time was 0.5 s, the confocal slit size was 120 μm, the accumulation number was 30, and the ND filter ratio was 16%. The Raman signal from miRNAs was processed through a spectrograph (interchangeable grating aberration free spectrograph, FEX) and a CCD camera (Newton 920, Andor Technology). Data analysis was conducted with SpectroLab 2.5 and Sigmaplot 10 software.

Results and Discussion

Fabrication of the Nanoplasmonic Biosensor (Head-Flocked Gold Nanopillar SERS Substrate)

Figure 2:
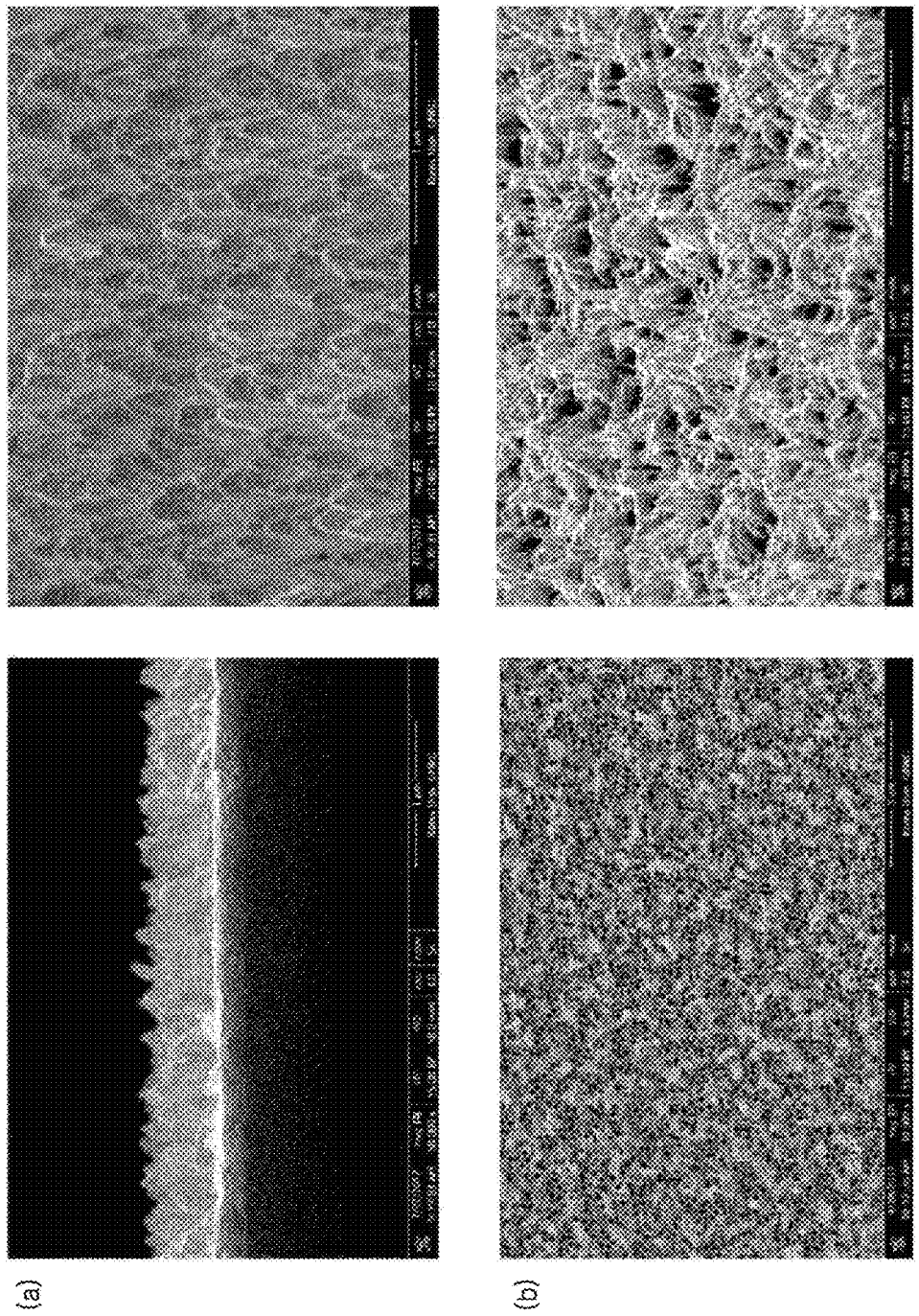
FIG. 2 shows (A) SEM images of the pure structure of gold nanopillars before sample treatment and (B) SEM images of the transformed structure of gold nanopillars conjugated with a capture part after sample treatment.

For multiplex and highly sensitive detection of several miRNAs, a head-flocked gold nanopillar SERS substrate (4 mm×4 mm) was produced using an elastic silicon nanopillar mold (FIG. 1). The head-flocked gold nanopillar structure was confirmed using a scanning electron microscopy (SEM) image (FIG. 2A). This structure was composed of uniform and mountaintop-shaped Si nanopillars arranged in lines. The height of the Si nanopillars was ~600 nm and the intervals between the Si nanopillars was ~200 nm. However, head-flocking of the top (head) portions of the gold nanopillars was observed in the head-flocked gold nanopillar substrate conjugated with the second DNA probe during the final process of sample treatment (FIG. 2B). This phenomenon occurred due to the elastocapillary force generated during liquid sample treatment. This force occurs when the liquid sample flows through a part of the nanopillar structure. The resulting head-flocked gold nanopillar structure generated SERS hotspots that resulted in a plasmonic coupling effect. Finally, an active and reproducible SERS nanostructure was successfully fabricated and the use of the cast slide glass established the basis for miRNA multiplex detection.

Figure 12:
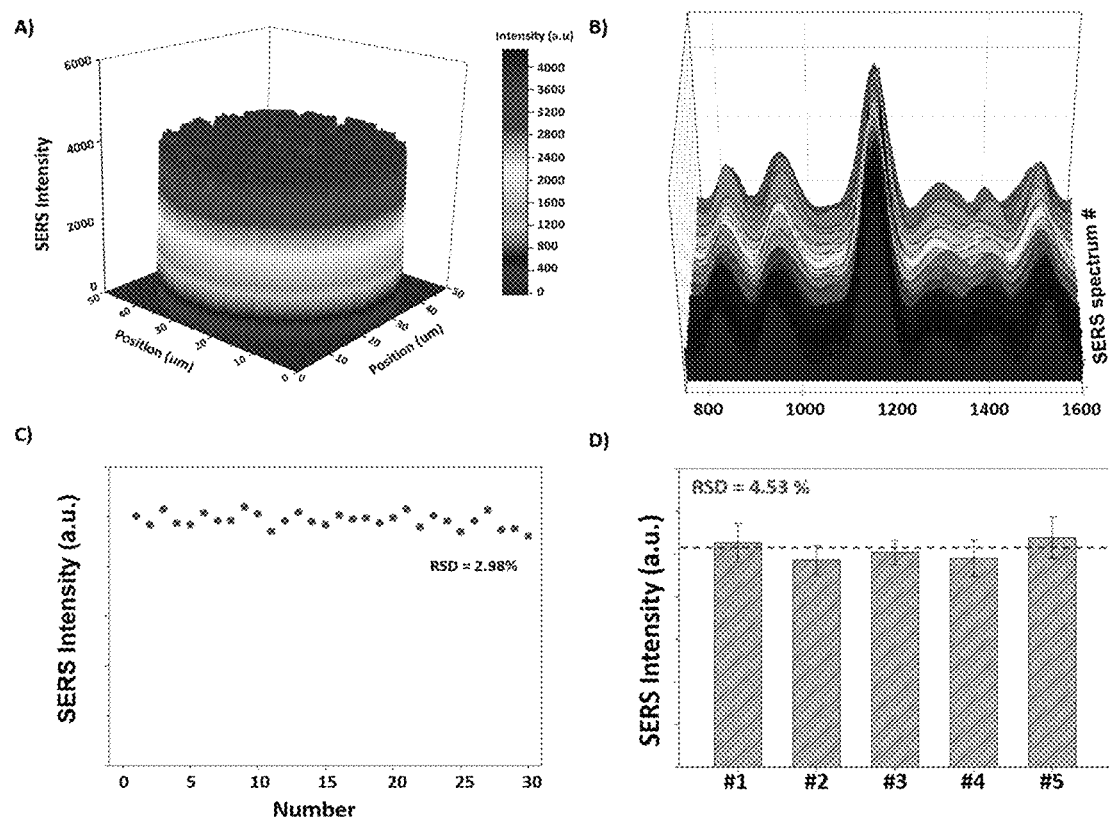
FIG. 12 shows uniformity of SERS signals over the entire area of a substrate: A) is a 3D representation of Raman mapping images in the presence of 100 nM miR-21. An area of 50 μm (X axis)×50 μm (Y axis) was scanned using an XY parallel stage. The scale bar at the right side of (A) indicates color decoding of Raman signal intensities; B) shows Raman spectra from 30 randomly selected spots of a SERS sensor; C) is a plot of corresponding Raman intensities of Cy3 signals at 1,150 cm$^{-1}$; and (D) shows the average Raman peak intensity distribution of Cy3 at 1,150 cm$^{-1}$ for 5 SERS sensors.
Figure 13:
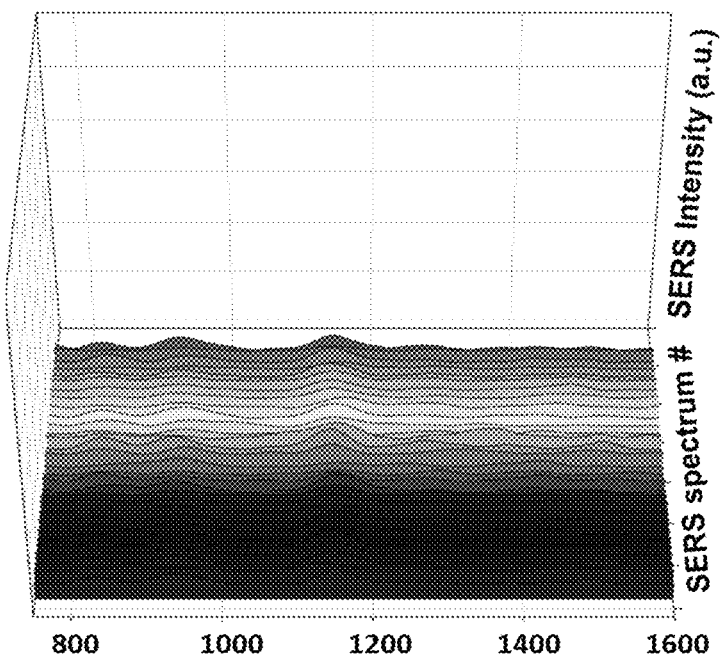
FIG. 13 shows SERS spectra and Cy3 intensities after hybridization with single-base mismatched miR-21A: (A) shows Raman spectra from 30 randomly selected spots of a SERS sensor; and (B) shows Raman intensities of Cy3 at 1,150 cm$^{-1}$.
Figure 13:
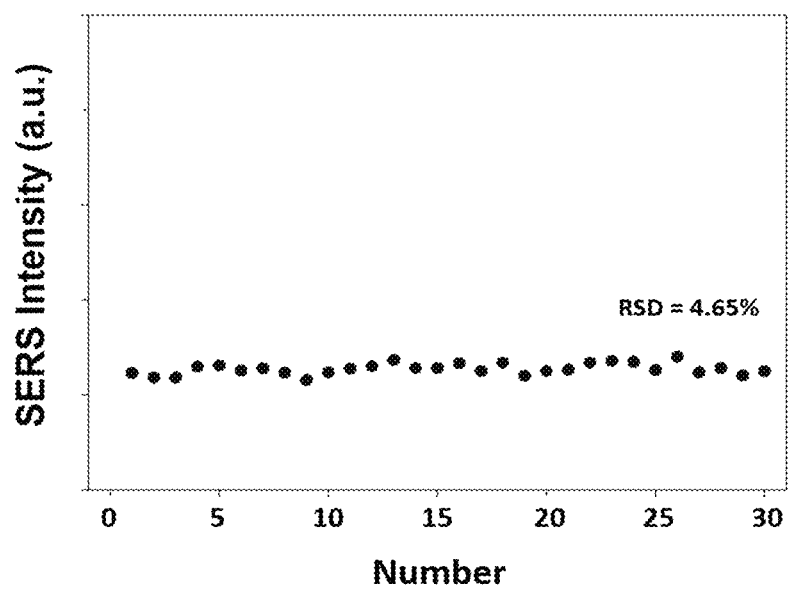

The uniformity of the SERS substrate is an important characteristic necessary for reproducible qualitative analysis of the target analytes. Raman mapping images of 100 nM miR-21 were measured and analyzed to evaluate the uniformity of the SERS substrate for exosomal miRNA detection (A) of FIG. 12). The SERS substrate was scanned with a mapping system at 1-μm intervals for a laser spot diameter of approximately 1 μm. As a result, a total of 2,500 pixels (1 pixel=1 μm×1 μm) were obtained for a square area and 1,964 pixels were imaged for a circular area of the SERS substrate. As shown in FIG. 12, SERS signal intensities were uniformly distributed over the entire area of the SERS substrate. In addition, SERS signals from 30 randomly selected spots of the sensor were recorded; and SERS spectra corresponding to Cy3 and SERS intensities at 1150 $cm^{-1}$ are shown in FIGS. 12B and 12C. According to the analytical results, the relative standard deviation (RSD) was 2.98%. The SERS spectra and Cy3 intensities after hybridization with the single-base mismatched miRNAs had a relative standard deviation of 4.65% (FIG. 13). These results demonstrate high uniformity of the plasmonic head-flocked gold nanopillar SERS-based sensor.

To verify the function of the inventive sensor for multiplex exosomal miRNA detection, 5 SERS sensors were fabricated using 100 nM miR-21 and their reproducibility was evaluated in the same manner as described above. The SERS signals for each sensor were measured at 30 different spots. The distribution of Raman peak intensities had a low RSD of 4.53% (D) of FIG. 12), showing very small changes in the SERS intensity of the 5 sensors. In conclusion, the SERS sensor of the present invention is suitable for qualitative detection of exosomal miRNAs while ensuring consistent reproducibility.

Signal Transition of miRNAs and Characterization of Fingerprint Peaks

DNA and RNA are composed of four types of bases having different chemical structures. When irradiated with a laser, the frequency of electrons varies depending on the sequence and percentages of bases in the chemical structures of DNA and RNA due to functional groups exposed to the surrounding and the double and triple hydrogen bonds between bases such as A-T and C-G. Based on such characteristics, Table 3 shows Raman signals assigned to the bonds between bases in the inherent chemical structures of DNA and RNA. Based on this principle, fingerprint peaks of miRNAs were identified and hybridization processes were monitored. To this end, signals were measured in a total of four separate steps.

TABLE 4

| Raman bonds ($cm^{-1}$) | Assignments |
| --- | --- |
| 640 | A, G, ring breathing |
| 825 | U, T ring breathing |
| 1167 | ($C_8H$, $N_{10}$—$H_{11}$), ($C_4$—$N_9$, $N_3$—$C_4$, $C_6$—$N_{10}$) |
| 1376 | $CH_3$, $C_6H$ deformation |
| 1521 | A, G |
| 1650 | T, C and $NH_2$ |

Figure 3:
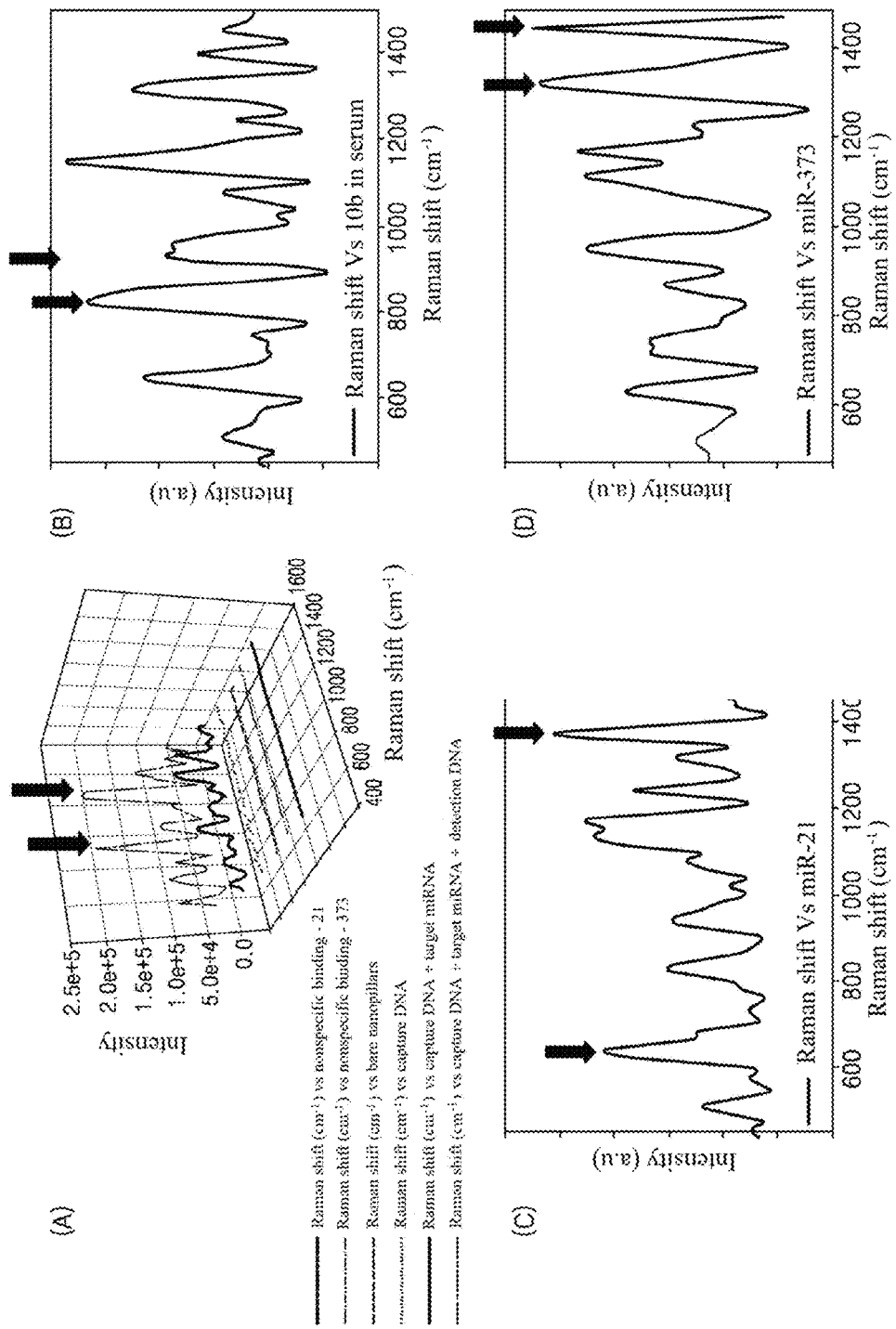
FIG. 3 shows (A) variations in Raman signal from bare gold nanopillars, gold nanopillars conjugated with a first DNA (capture DNA), gold nanopillars conjugated with a first DNA (capture DNA) hybridized with target miR-10b, and gold nanopillars conjugated with a second DNA and a first DNA (capture DNA) hybridized with target miR-10b, (B) a Raman spectrum of gold nanopillars conjugated with a second DNA and a first DNA (capture DNA) hybridized with target miR-10b at a serum concentration of 100 nM, (C) a Raman spectrum of gold nanopillars conjugated with a second DNA and a first DNA (capture DNA) hybridized with target miR-21 at a serum concentration of 100 nM, and (D) a Raman spectrum of gold nanopillars conjugated with a second DNA and a first DNA (capture DNA) hybridized with target miR-373 at a serum concentration of 100 nM.

The entire procedure was carried out in human serum. First, the SERS substrate was examined for the presence or absence of background signals. To this end, SERS signals from the bare gold nanopillar substrate were examined Second, changes in SERS signals from the gold nanopillars conjugated with the first DNA were examined No noticeable signal variation was observed in the bare gold nanopillar structure. The first DNA probe conjugated with the gold nanopillars existed in the form of single-stranded DNA (10-12 nt). Since there were no bonds between the bases of the first DNA probe, no signals other than the inherent signals from the bases were generated. As a result, no significant changes in signal intensity were observed. However, a larger number of bases were present around the head-flocked gold nanopillar structure when the target miRNA was hybridized with the first DNA probe (head-flocking) than when the nanopillar structure was treated with the first DNA probe only. In addition, new bonds were formed between the bases, which had not been observed in the previous step, and as a result, signals with increased intensity were noticeably generated. The number of bases present around the head-flocked gold nanopillar structure increased compared to before the process and bonds were formed between the bases. As shown in (A) of FIG. 3, the second DNA probe was hybridized with the target miRNA and signal variations were confirmed to observe whether complete hybridization between the DNA probe and the target miRNA occurred. As a result, the same SERS signal trends as those before hybridization were verified. The signal intensity was amplified by 10-20 fold compared to that of the gold nanopillars before hybridization of the second DNA with the target miRNA. These results demonstrate that there are fingerprint peaks for the miRNAs and the inventive nanoplasmonic biosensor (head-flocked gold nanopillar DNA chip) has the ability to monitor the hybridization. This procedure was repeated to identify fingerprint peaks for each miRNA. The fingerprint peaks of miR-10b were measured at 825 $cm^{-1}$ and 1167 $cm^{-1}$ (FIG. 3B). The fingerprint peaks of miR-21 were measured at 640 $cm^{-1}$ and 1376 $cm^{-1}$ (FIG. 3C). The fingerprint peaks of miR-373 were measured at 1521 $cm^{-1}$ and 1650 $cm^{-1}$ (FIG. 3D). These results demonstrate that the nanoplasmonic biosensor of the present invention is capable of label-free detection of the target miRNA with high selectivity.

Figure 9:
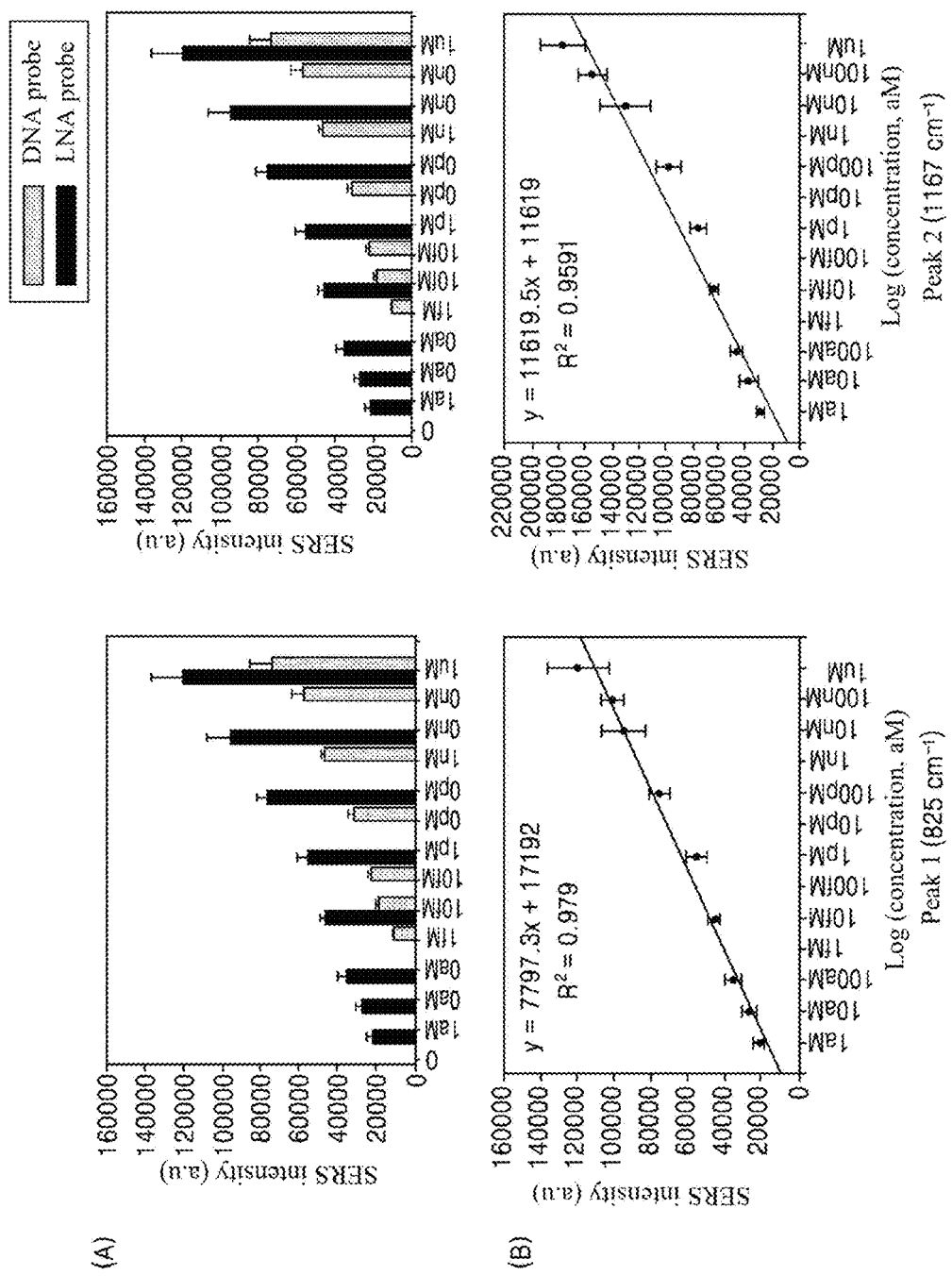
FIG. 9 compares SERS intensities and linear regression curves obtained when a DNA and an LNA, each including a sequence complementary to miR-10b, were used.

In addition, an experiment was conducted using a locked nucleic acid (LNA) probe that is a highly sensitive gene probe in surface-enhanced Raman scattering. miR-10b was used as the target miRNA. LNA is a nucleic acid that exhibits more potent affinity than the corresponding DNA or RNA. LNA has a chemical structure in which 2'-O and 4'-C atoms are connected via a methylene bridge. Due to this structure, LNA has an ideal conformation for Watson-Crick binding. (A) of FIG. 9 shows SERS intensities obtained when different concentrations of the target miR-10b were hybridized with the LNA and DNA probes. The SERS intensities were found to be about 4-5 times higher than that of the DNA probe. In addition, the limits of detection were 100 times lower than that of the DNA probe (FIG. 9B).

Evaluation of Nonspecific Binding Between Target miRNAs

Figure 4:
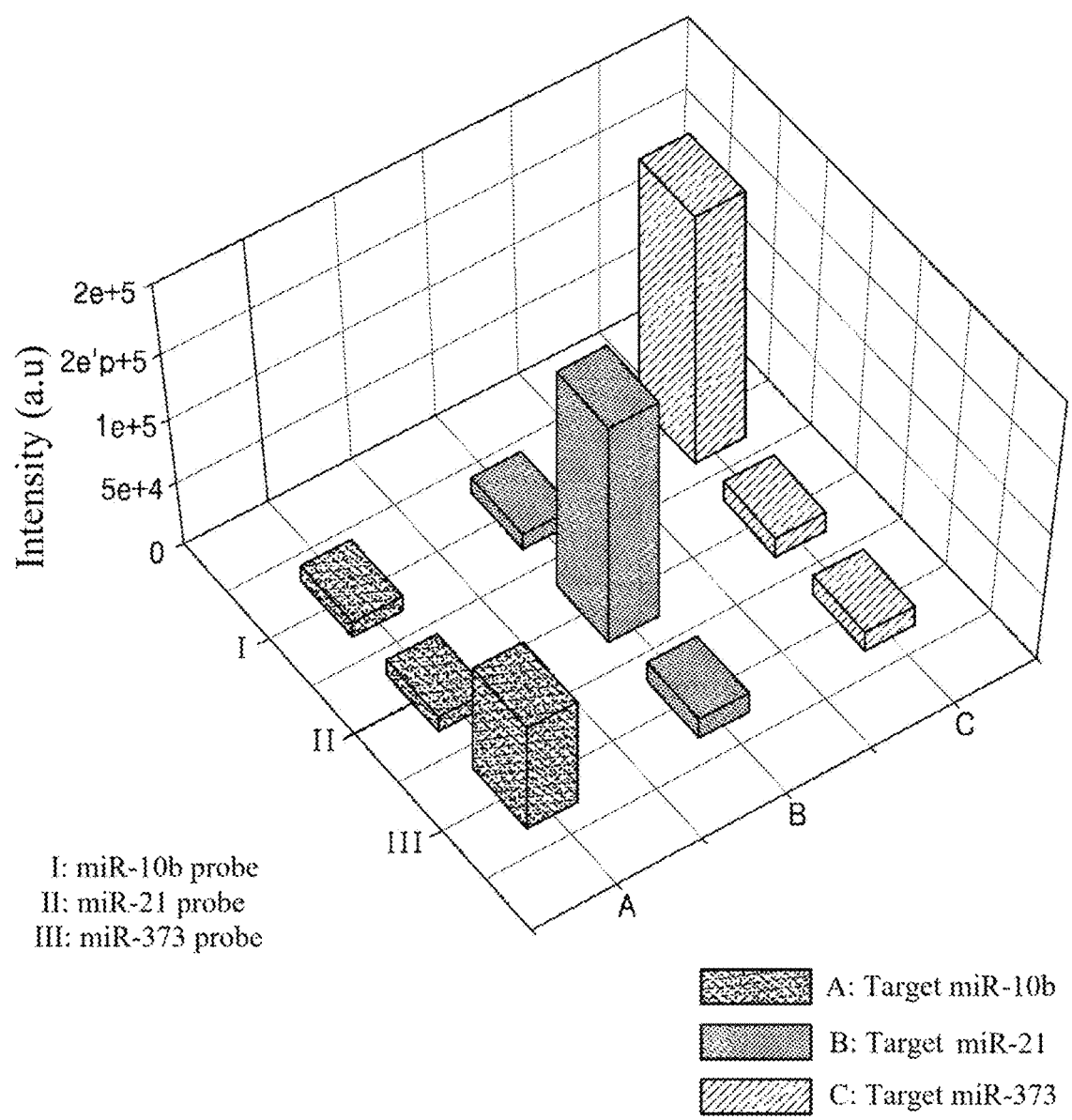
FIG. 4 shows Raman signal intensities of a nanoplasmonic biosensor according to the present invention for the evaluation of nonspecific binding to miR-10b, miR-21, and miR-373 at peak 2.
Figure 6:
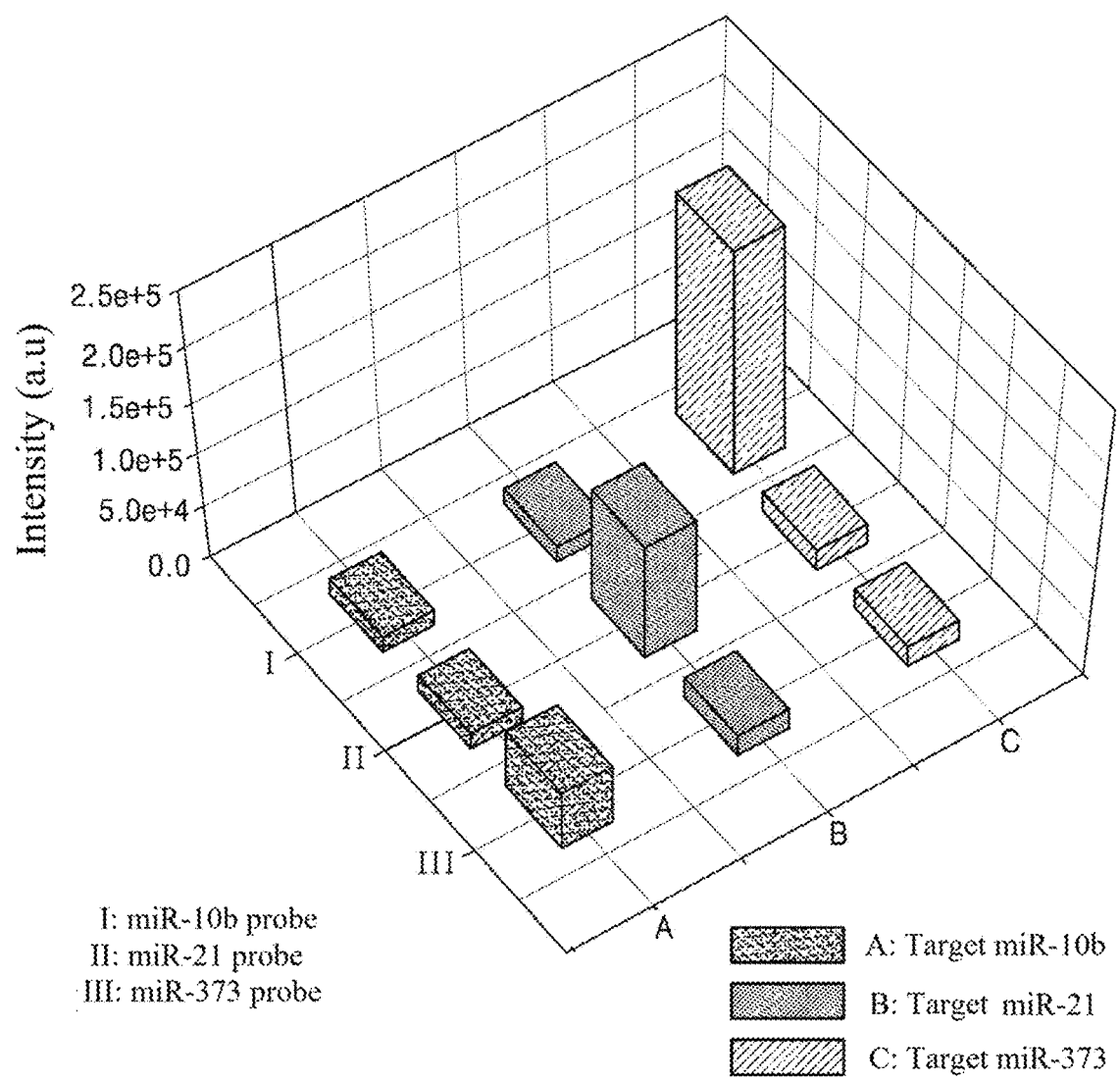
FIG. 6 shows Raman signal intensities of a nanoplasmonic biosensor according to the present invention for the evaluation of nonspecific binding to miR-10b, miR-21, and miR-373 at peak 1.

One major issue of biosensors for multiplex detection is crosstalk between analytes (Porter M. D., Lipert R. J., Siperko L. M., Wang G. and Narayanan R., 2008. Chem. Soc. Rev., 37, 1001-1011). This phenomenon often occurs between transformation markers. In the present experiment, no markers were used to exclude the occurrence of crosstalk but a similar limitation existed. Indeed, since several miRNAs circulate in the bloodstream, it is essential to evaluate nonspecific binding of DNA probes to mismatched miRNAs. For this reason, other non-complementary miRNAs were hybridized with the DNA probe and the intensities of fingerprint peaks for each miRNA were examined. In FIG. 4 (peak 2) and FIG. 6 (peak 1), two 3-dimensional vertical histograms are shown. When the miRNA fingerprint peaks were aligned, the peak closest to 0 $cm^{-1}$ was designated as peak 1 and the second closest peak was designated as peak 2. Each graph compares target miRNA intensities at the fingerprint peak. High signal intensities were observed at the fingerprint peaks only in the DNA probes complementary to the corresponding miRNAs. These results confirm that only the complementary DNA probes bind to the corresponding target miRNAs. That is, the nanoplasmonic biosensor of the present invention is capable of label-free multiplex detection of cancer biomarkers with high selectivity.

Figure 10:
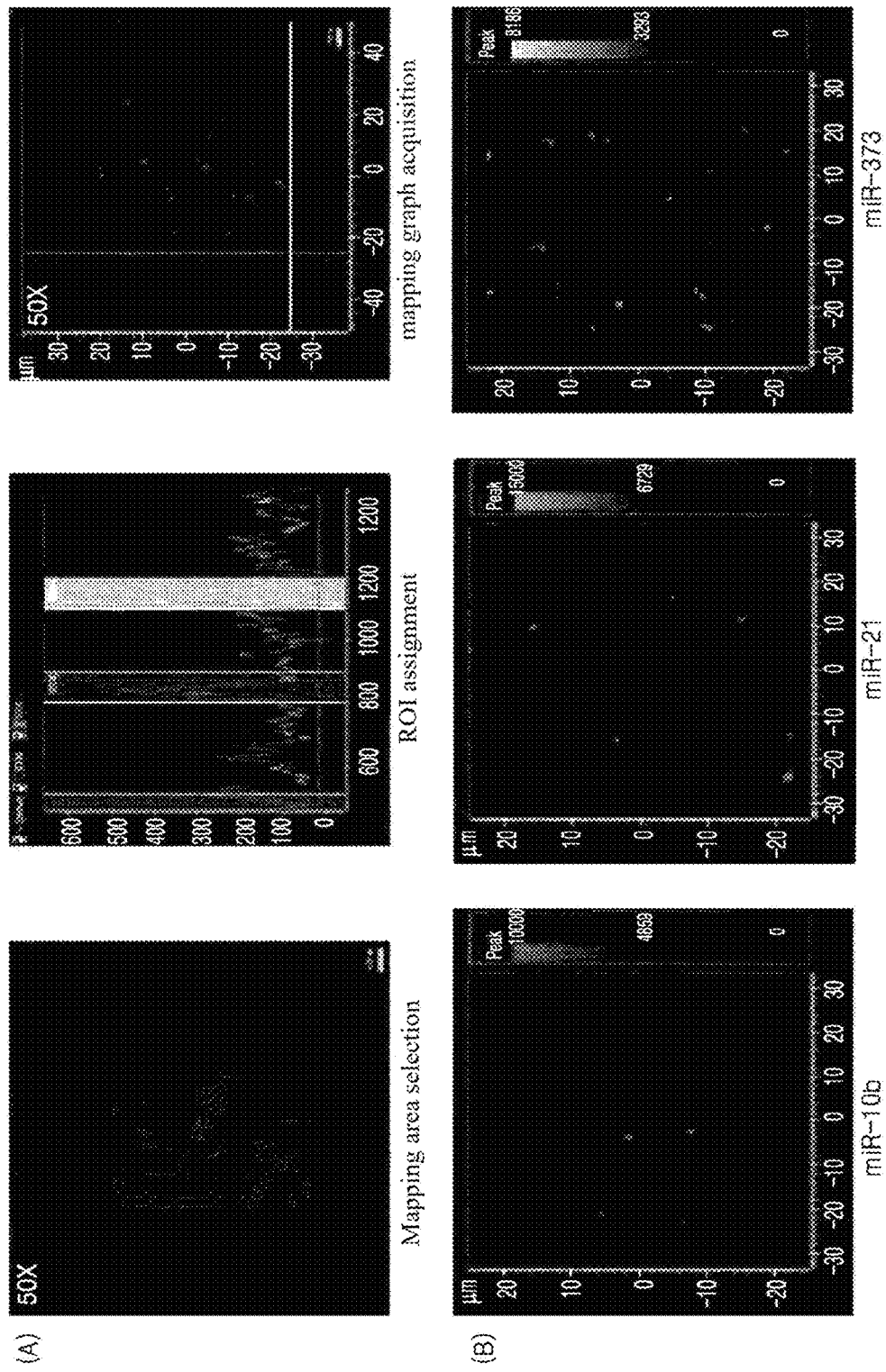
FIG. 10 shows (A) a Raman mapping method (mapping area selection, ROI (region of interest) assignment at a fingerprint peak, and acquisition of a mapping graph in the mapping area) and (B) mapping graphs for miRNAs at fingerprint peaks.
Figure 11:
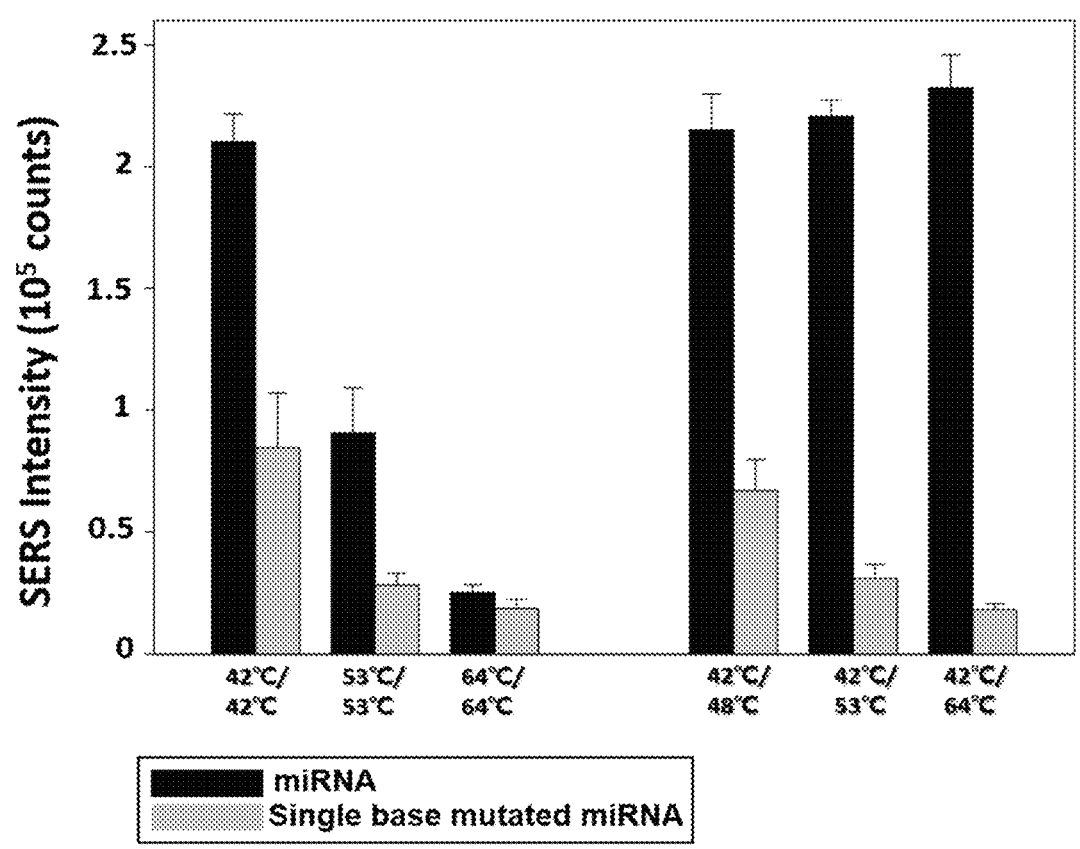
FIG. 11 shows Cy3 SERS intensities at 1,150 $cm^{-1}$ after hybridization with target miR-21 and single-base mismatched miR-21B (100 nM) at different temperatures. The temperatures shown at the top were used for hybridization with the target miRNAs and the temperatures shown at the bottom were used for LNA detection probes. Each error bar represents the standard deviation of 20 determinations.
Figure 14:
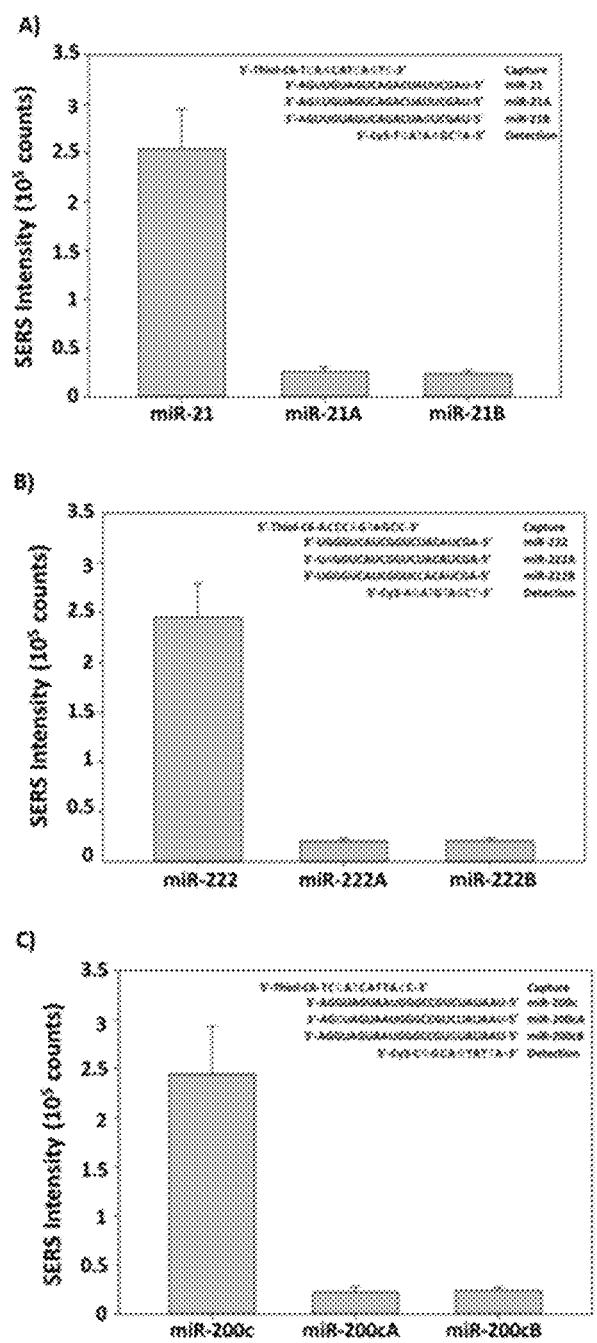
FIG. 14 shows the selectivities of a sensor to various target miRNAs. Strong SERS signals were produced by only perfectly matched target miRNAs with miR-21 (A), miR-222 (B) and miR-200c (C) and were not produced by miRNAs containing single-nucleotide mismatches (miR-21A and B, miR-222A and B, and miR-200cA and B). The sequences of target miRNAs and LNA capture and detection probes are shown in each panel. Each error bar represents the standard deviation of 20 determinations.
Figure 15:
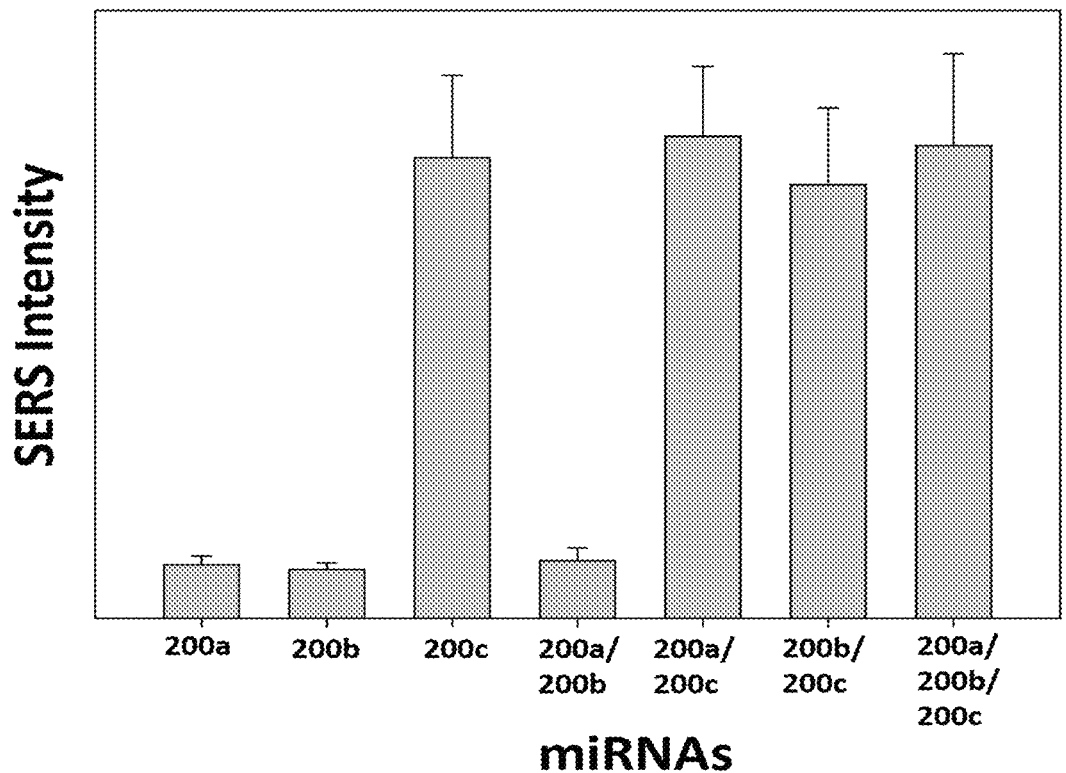
FIG. 15 shows Cy3 SERS intensities from a SERS sensor hybridized with 1, 2 or 3 miRNAs of the miR-200 family (100 nM) at 1,150 cm$^{-1}$. Each error bar represents the standard deviation of 20 determinations.

On the other hand, a sensor for miRNA detection should have high selectivity to sequentially distinguish similar miRNAs. Perfectly matched target miRNAs and two miRNAs (types A and B) with unsuitable bases at the LNA capture and detection probe recognition sites were used to evaluate the selectivity of the inventive sensor. SERS signal intensities of Cy3 between the perfectly matched miRNAs and the single-base mismatched miRNAs at 1150 $cm^{-1}$ were compared (FIG. 14). The concentration of all miRNAs was 100 nM. The SERS signal intensities were not significant in the presence of all single-base mismatched miRNAs (types A and B), whereas strong SERS signal intensities were observed in the presence of the perfectly matched miRNAs. In the present invention, the single-base mismatched miRNAs were perfectly distinguished by breaking the unstable single-base mismatched miRNA-LNA hybridization structures at temperatures of $T_m$ or above during miRNA detection. In addition, the detection capability of the SERS sensor was demonstrated using the miR-200 family (miR-200a, miR-200b and miR-200c) in human serum. FIG. 15 shows SERS signal intensities of Cy3 (1,150 $cm^{-1}$) in various combinations of miRNAs in the miR-200 family Raman Mapping Process for Formation of Head-Flocked Hotspots The inventive SERS-based nanoplasmonic biosensor using the head-flocked gold nanopillar matrix was subjected to Raman mapping to monitor the Raman signal in a particular range. As shown in (A) of FIG. 10, each of the X and Y axes was divided into 50 equidistant points such that the distance between the two adjacent points was 1 μm. The entire area (2500 μm$^2$) was mapped twice. Each sub-area (1 μm×1 μm) was designated as one coordinate region. The Raman signal from each region was measured. The signal intensities of all regions were summarized to distinguish the regions where the Raman signals were high from the regions where the Raman signals were low. That is, only the regions where the signal intensities were within the top 10% were selected. The selected regions were plotted to obtain Raman mapping graphs ((B) of FIG. 10). Based on these results, spots with high signal intensity were selected (n=20) and the averages and standard deviations of the Raman signal intensities were determined. As a result of this Raman mapping, the locations of the head-flocked gold nanopillars and the regions where the signals were strongly amplified could be selected, which reduces the error range of quantitative analysis and ensures high accuracy.

Relative Quantitative Analysis of Target miRNAs

The sensitivity the nanoplasmonic biosensor was evaluated by performing the quantitative analysis of three target miRNAs using patient-mimicking serums as model analytes under optimal conditions. The relative quantitative analysis of the target miRNAs was conducted by measuring SERS signal intensities at various concentrations of the target miRNAs.

Figure 5:
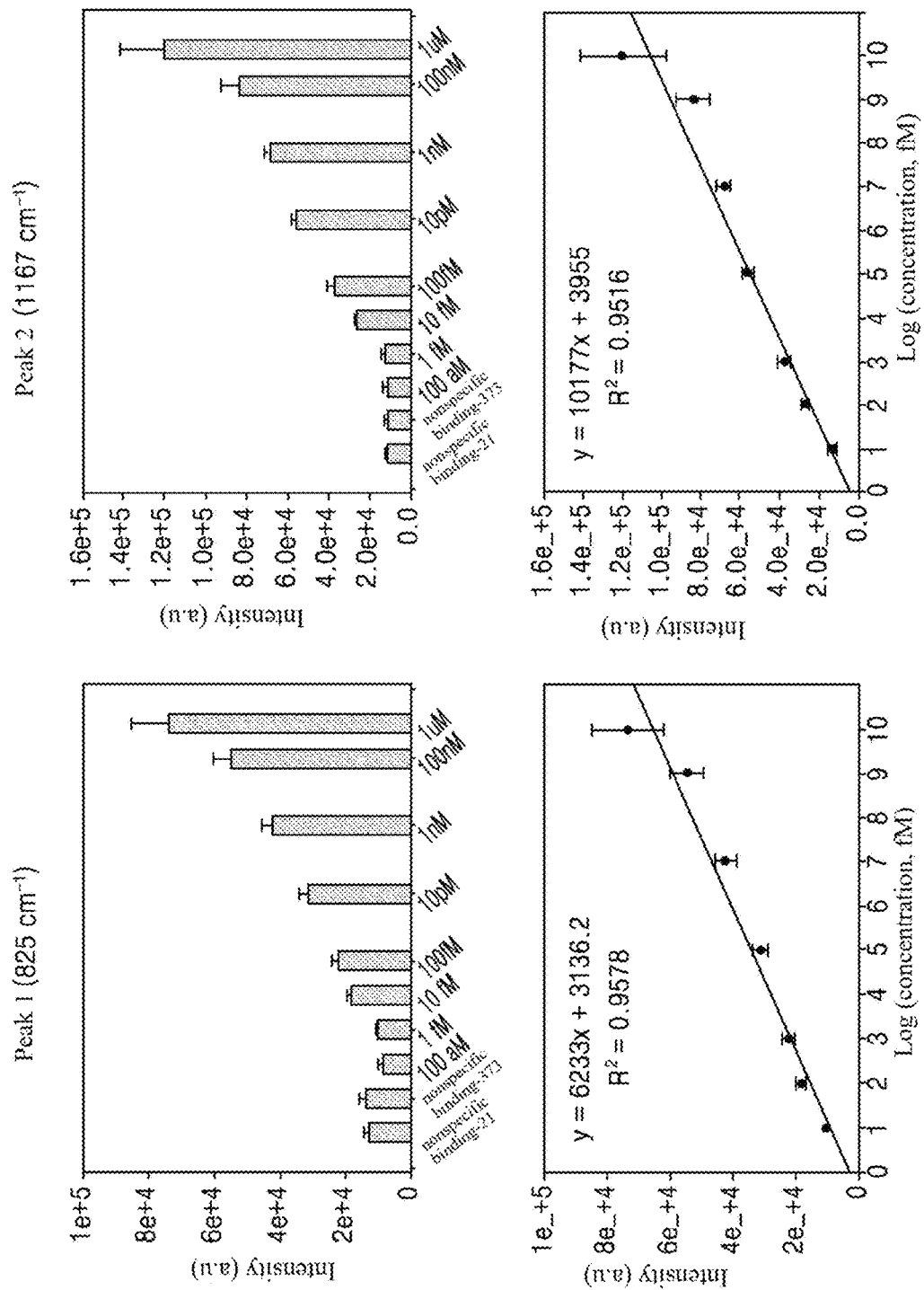
FIG. 5 shows variations in SERS signal intensity at each peak in response to the concentration of target miR-10b in patient-mimicking serums as model analytes.
Figure 7:
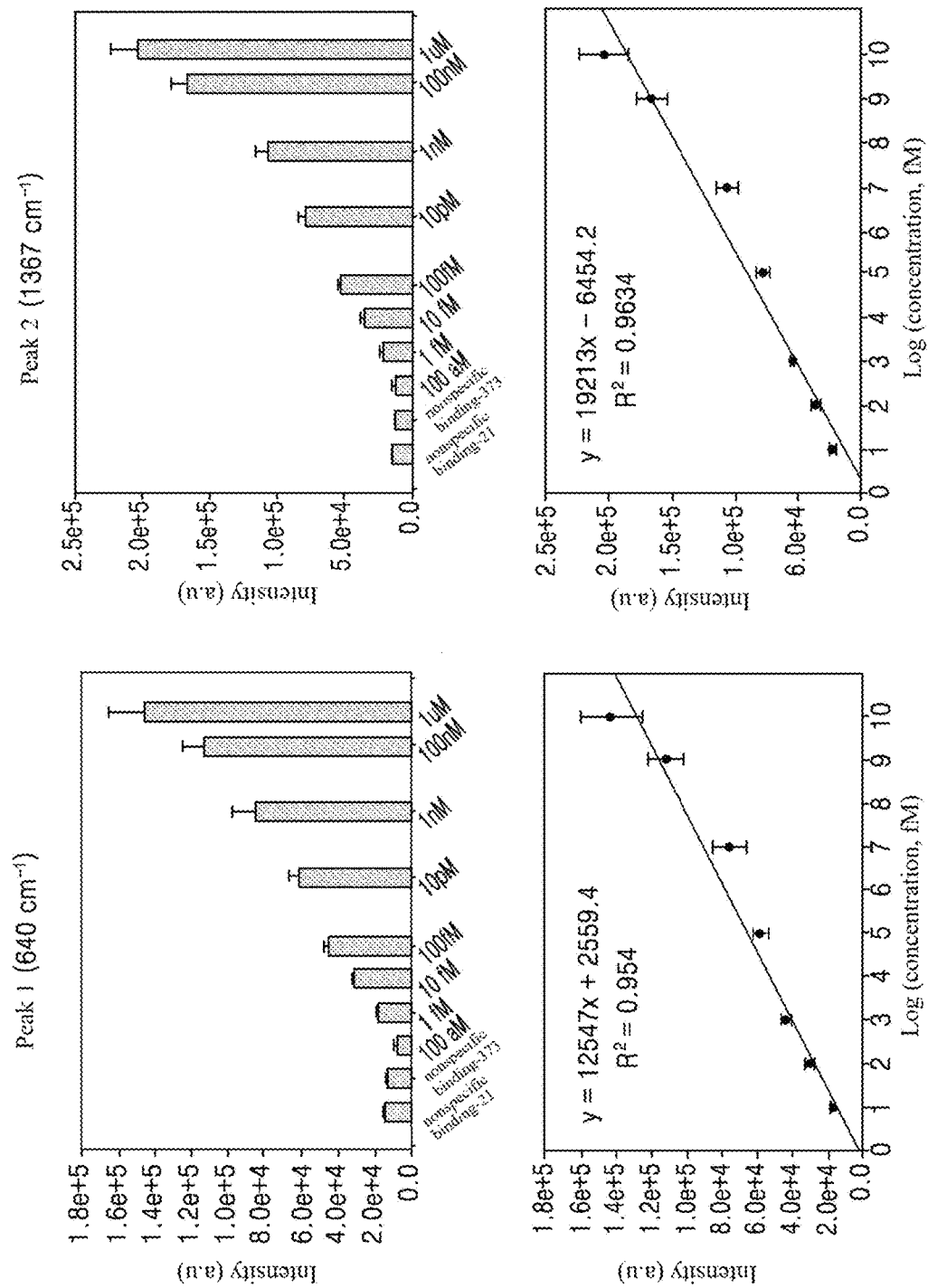
FIG. 7 shows variations in SERS signal intensity at each peak in response to the concentration of target miR-21 in patient-mimicking serums as model analytes.
Figure 8:
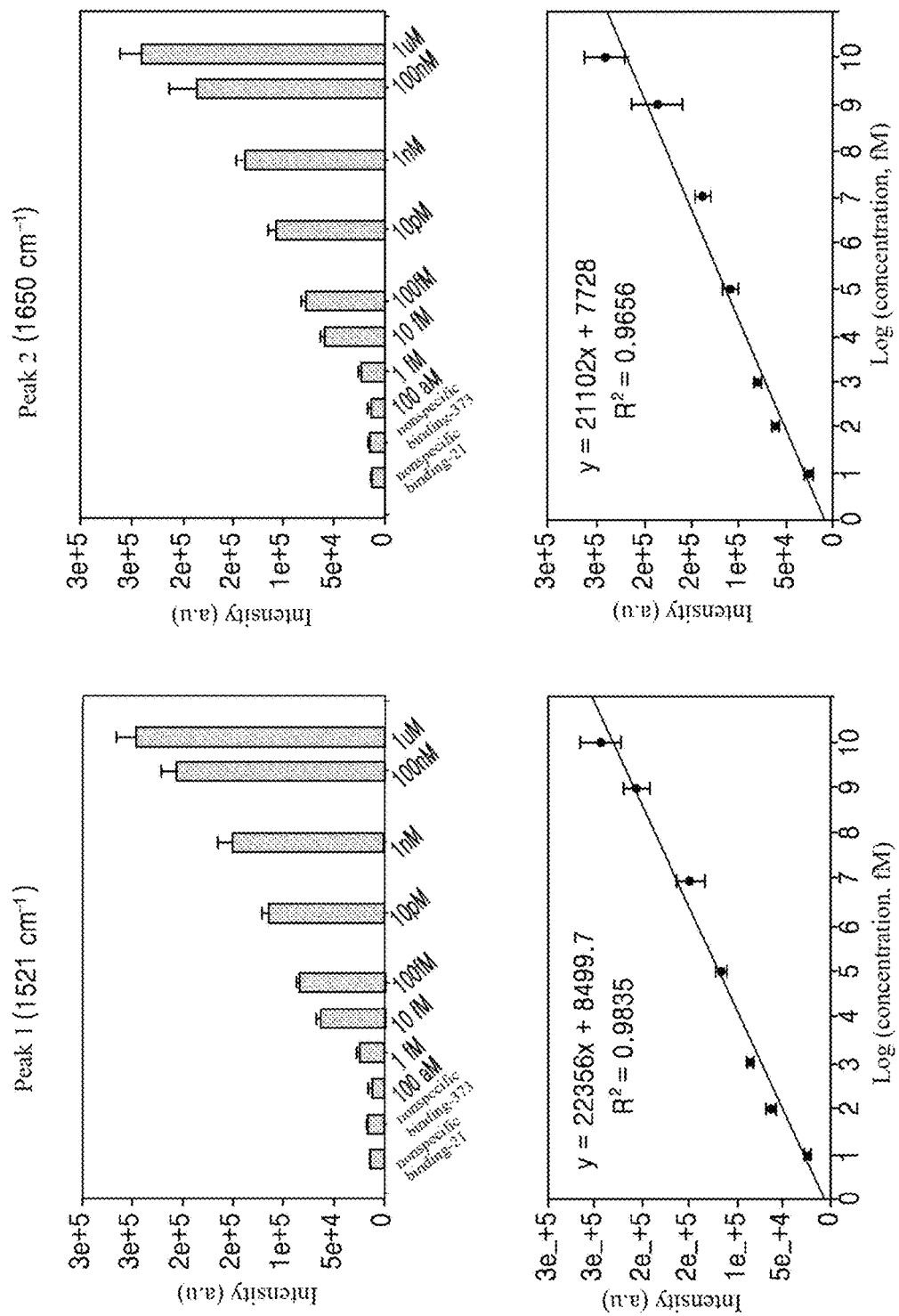
FIG. 8 shows variations in SERS signal intensity at each peak in response to the concentration of target miR-373 in patient-mimicking serums as model analytes.

As shown in (a) of FIG. 5, the quantitative analysis was performed in the concentration range of 1 μM to 100 aM and for blank samples (nonspecific binding). In addition, the reliability of the limit of detection was estimated by comparing the intensity at each concentration with that at the nonspecific binding. As a result, the SERS signal intensity had a strong logarithmic linear regression relationship with the target miRNA concentration, as shown in (b) of FIG. 5. From the graphs, linear regression equations and coefficients of determination were verified. Normally, the coefficient of determination is an important factor in assessing the correlation between dependent and independent variables in statistics; thus, the higher the coefficient of determination, the greater the reliability of the correlation between the two variables. The coefficients of determination obtained for the target miRNAs were 0.974 (peak 1) and 0.959 (peak 2) for miR-10b ((B) of FIG. 5), 0.97 (peak 1) and 0.963 (peak 2) for miR-21 (FIG. 7), and 0.984 (peak 1) and 0.966 (peak 2) for miR-373 (FIG. 8).

The fact that the coefficients of determination are between 0.95 and 0.98 reveals that the nanoplasmonic biosensor of the present invention is highly sensitive and the concentration of each target miRNA is closely related to the SERS signal intensity. No fingerprint peaks were found at 100 aM and the signal intensities at the fingerprint peaks were similar to those at the nonspecific binding. Based on these findings, approximate limits of detection could be determined.

The exact limit of detection (LOD) values of the inventive nanoplasmonic biosensor were calculated using the formula LOD=$(3\times\delta)$/m where $\delta$ is the standard deviation of the nonspecific binding and m is the gradient of the linear regression equation (Gracie K., Correa E., Mabbott S., Dougan J. A., Graham, D. Goodacre R. and Faulds K., 2014, Chem. Sci. 5, 1030-1040). The calculated LOD values were 5.46 fM (peak 1) and 3.53 fM (peak 2) for miR-10b, 3.16 fM (peak 1) and 2.08 fM (peak 2) for miR-21, and 1.73 fM (peak 1) and 2.16 fM (peak 2) for miR-373.

As described above, the nanoplasmonic biosensor of the present invention has a very high sensitivity on the order of fM and a low limit of detection, demonstrating its high potential to clinically apply to miRNA-related diseases.

Figure 16:
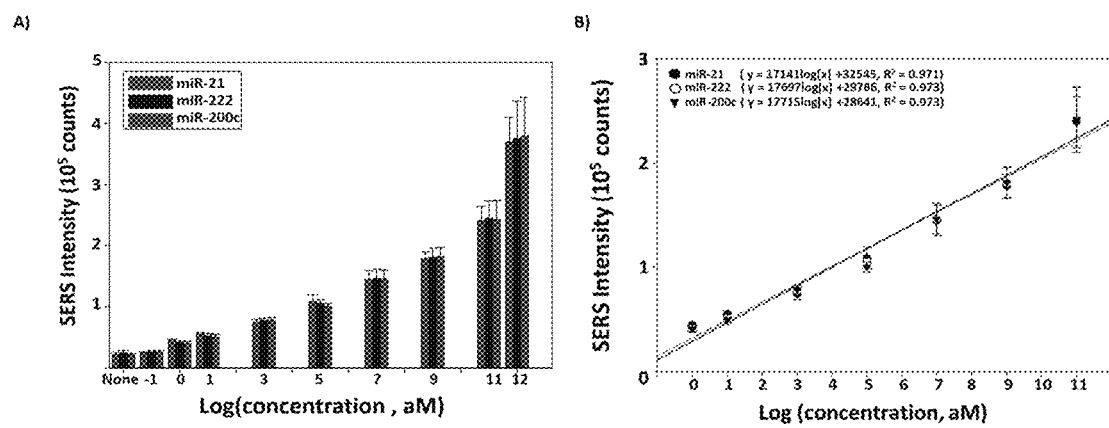
FIG. 16 shows the sensitivities of a SERS sensor for detecting target miRNAs: (A) is a plot of Cy3 intensities at 1,150 cm$^{-1}$ versus the concentrations of target miRNAs (miR-21, miR-222 and miR-200c); and (B) shows the results of linear regression analysis explaining the relationship between the Cy3 intensities and the concentrations of the target miRNAs (x, miRNA concentration). Each error bar represents the standard deviation of 20 determinations.

Next, the SERS spectra and SERS band intensities of Cy3 were analyzed based on the concentrations of the target miRNAs. As a result, Cy3 specific SERS signals were detected at extremely low concentrations (~1 aM) of the target miRNAs. Despite the different sequences of the target miRNAs, the SERS signal intensities of the miRNAs increased gradually in a concentration-dependent manner and increased linearly in the broad concentration range of 1 aM to 100 nM. The limit of detection was predicted to be 1 aM even without the need for amplification. When the Cy3 intensities were normalized to the concentrations of the target miRNAs, the linear responses of the SERS sensor were confirmed (FIG. 16). The linear regression equations were determined as follows:

$$y=17141 \log(x)+32545 \ (R^2=0.972) \text{ for miR-21,}$$

$$y=17697 \log(x)+29786 \ (R^2=0.973) \text{ for miR-222, and}$$

$$y=17715 \log(x)+28641 \ (R^2=0.973) \text{ for miR-200c,}$$
where $x$ is miRNA concentration.

In all calibration curves, the SERS intensities showed a strong linear relationship with the logarithmic concentrations of the target miRNAs.

Figure 18:
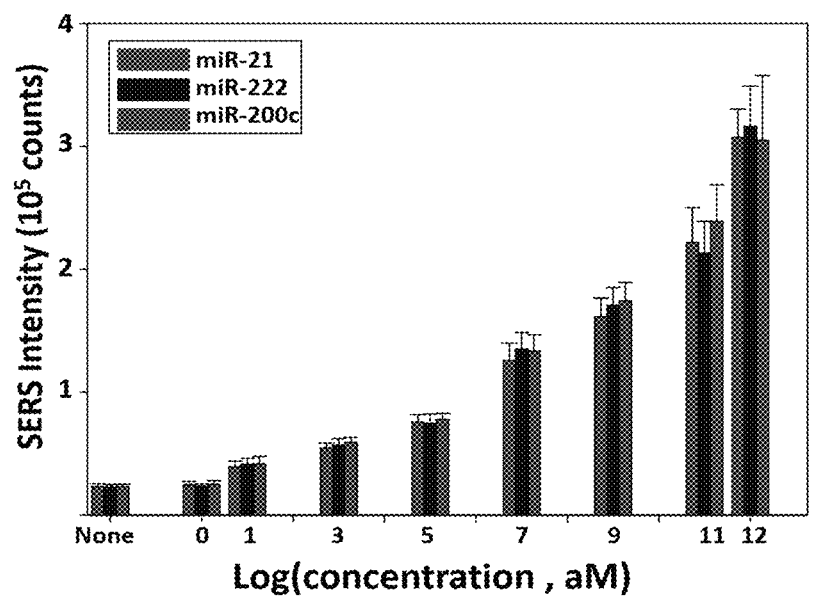
FIG. 18 shows the ability of a SERS sensor to detect target miRNAs in human serum: (A) shows Cy3 fluorescence intensities at 1,150 cm$^{-1}$ in the presence of indicated concentrations of target miRNAs (miR-21, miR-222 and miR-200c) in human serum; and (B) shows the results of linear regression analysis explaining the relationship between the SERS intensities of Cy3 and the concentrations of the target miRNAs in human serum (x, miRNA concentration). Each error bar represents the standard deviation of 20 determinations.
Figure 18:
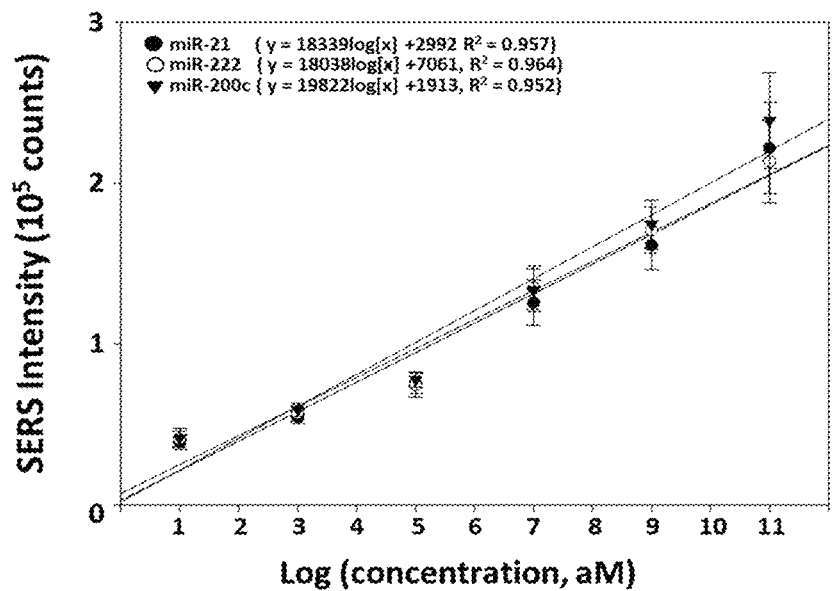

To verify the effect of this method in a biologically relevant context, the sensor of the present invention was applied to the detection of target miRNAs diluted in human serum. As a consequence, Cy3 signal intensities increased linearly in the miRNA concentration range of 10 to 100 nM (FIG. 18) corresponding to the content of exosomal miRNAs in patient serum. The linear regression equations are as follows:

$$y=18339 \log(x)+2992 \ (R^2=0.957) \text{ for miR-21,}$$

$$y=18038 \log(x)+7061 \ (R^2=0.964) \text{ for miR-222, and}$$

$$y=19822 \log(x)+1913 \ (R^2=0.952) \text{ for miR-200c,}$$
where $x$ is miRNA concentration.

In all calibration curves for the miRNA contents in human serum, the SERS intensities showed a good linear relationship with the logarithmic concentrations of the target miRNAs. These results suggest that the SERS sensor of the present invention can effectively detect miRNAs in human serum.

Detection of Exosomal miRNAs Released from Breast Cancer Cells

Figure 17:
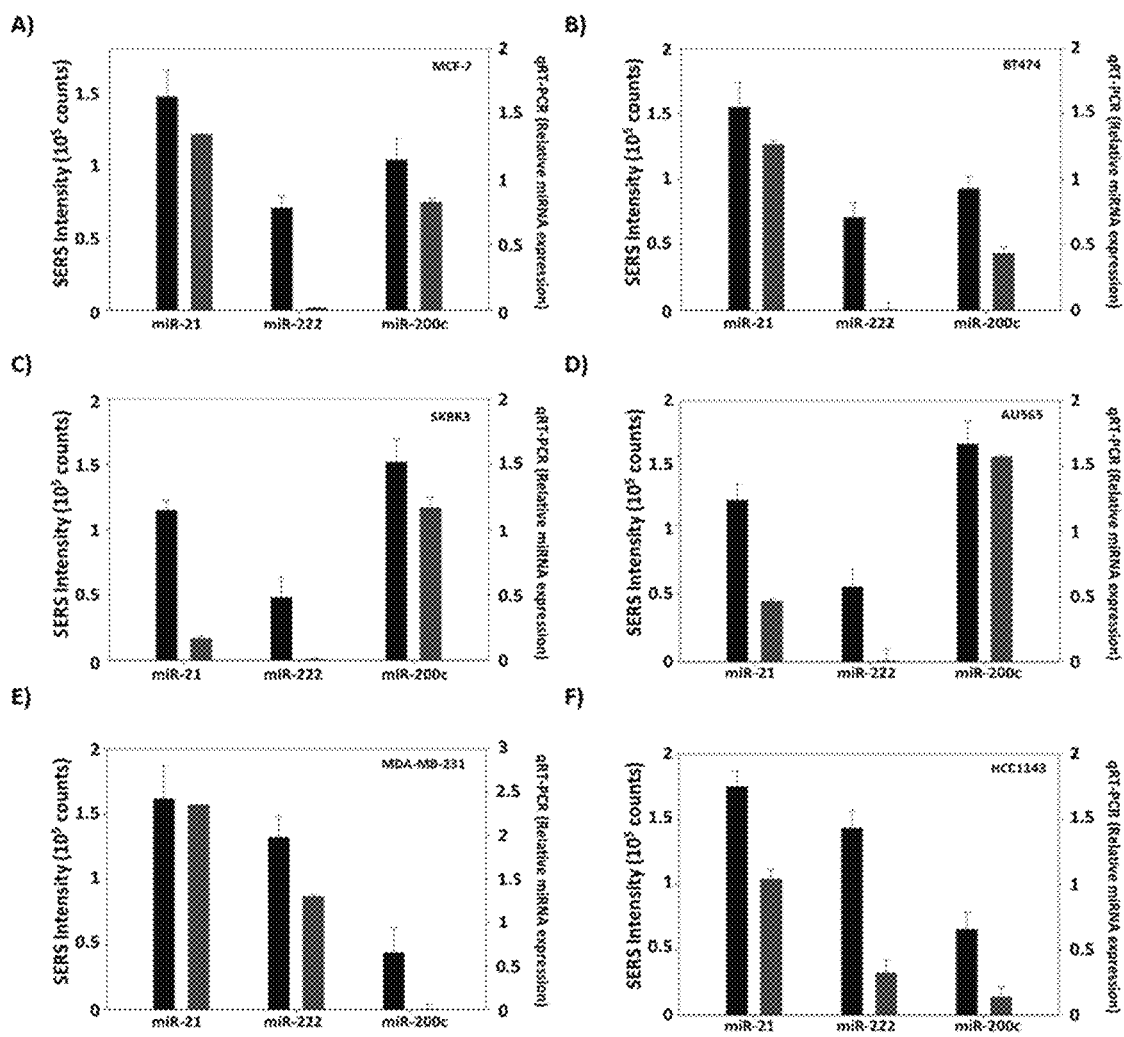
FIG. 17 shows the levels of exosomal miRNAs in different breast cancer subtypes. The levels of target exosomal miRNAs (miR-21, miR222 and miR-200c) in various breast cancer subtype cell lines were determined by a SERS sensor (blue bars) and qRT-PCR (red bars). The breast cancer subtypes were A) and B) luminal subtypes (MCF-7 and BT474), C) and D) HER2$^+$ subtypes (SKBR3 and AU565), and E) and F) TN subtypes (MDA-MB-231 and HCC1143). Each Y axis represents SERS intensities and each X axis represents qRT-PCR results (relative exosomal miRNA expressions). The error bars represent the standard deviations of 20 determinations for SERS and the standard deviations of 3 determinations for qRT-PCR.
Figure 19:
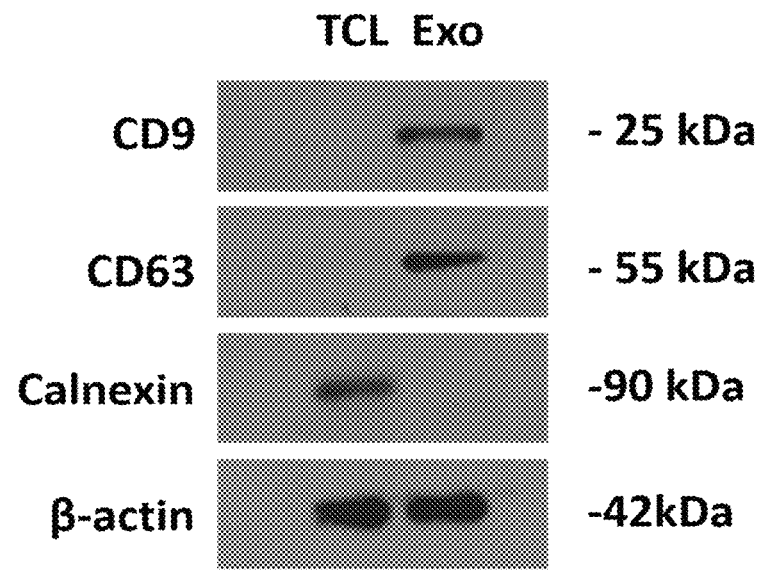
FIG. 19 shows the protein expression and morphology of exosomes secreted from breast cancer cells: (A) shows the results of Western blotting of total cell lysates (TCL) and exosomes (20 μg/lane) for CD9, CD63, and calnexin expression. The molecular weights of the proteins are shown at the right side of (A); and (B) is a transmission electron microscopy image of exosomes (scale bar, 100 nm).
Figure 19:
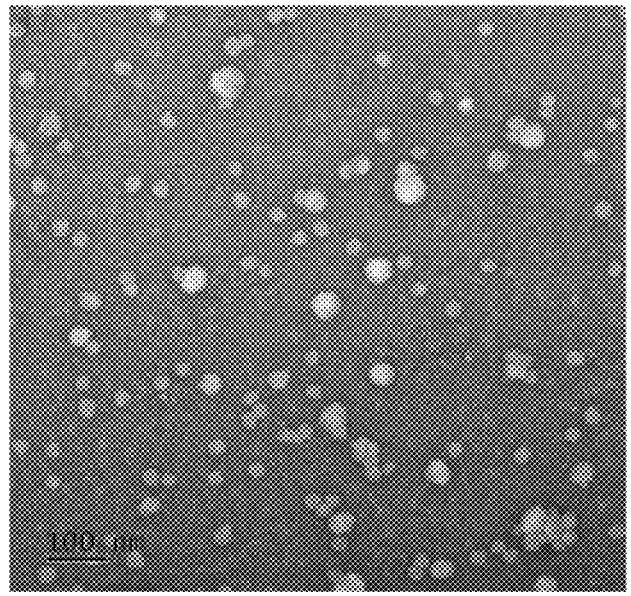

Exosomal miRNAs exhibit considerable stability and are present in different levels in the biofluids of breast cancer patients and healthy individuals. For these reasons, exosomal miRNAs are ideal candidate biomarkers for malignant tumors, particularly breast cancer. Accordingly, the identification of exosomal miRNAs in biofluids would be a promising diagnostic method for clinical purposes. The levels of three types of miRNAs in exosomes derived from three breast cancer subtypes (luminal, HER2+, and TN) from breast cancer cell lines were investigated to test the applicability of the biosensor to breast cancer diagnosis. Exosomes released into cell culture media were purified and their protein expression and morphology were analyzed (FIG. 19). The expression of exosomal surface markers CD9 and CD63 was confirmed by Western blotting (A) of FIG. 19). Transmission electron microscopy revealed that the purified exosomes were round in shape and had a diameter in the range of 30 nm to 100 nm (FIG. 19). Next, exosomal miRNAs were extracted from breast cancer cell lines and the expression levels of the purified exosomal miRNAs were measured using the SERS sensor of the present invention and qRT-PCR. As shown in FIG. 17, the detection results obtained using the SERS sensor of the present invention were in good agreement with the results obtained using qRT-PCR. The SERS signals clearly showed that exosomal miRNAs (miR-21, miR-222 and miR-200c) showed different expression profiles in the breast cancer subtypes.

In addition, the expression of miR-21 was found to be significantly high in the breast cancer subtypes luminal and TN compared to the breast cancer subtype HER2$^+$. The expression profiles of miR-222 and miR-200c could be clearly distinguished depending on the breast cancer subtype. As a result of analysis using the SERS sensor and qRT-PCR, it was observed that a higher level of miR-222 was detected in the breast cancer subtype TN than in the other breast cancer subtypes but a high level of miR-200c in the breast cancer subtype HER2$^+$ was clearly observed. These results suggest that the SERS sensor of the present invention can accurately detect exosomal miRNAs in breast cancer cell lines and can distinguish the breast cancer subtypes according to the expression pattern of exosomal miRNAs.

To investigate the practical applicability of the SERS sensor, a recovery test was conducted by adding known concentrations of miR-21, miR-222 and miR-200c to human serum. Table 5 shows that the recovery values are in the allowable range (97-102%). In addition, the RSDs for the three target miRNAs are in the range of 3% to 6%, indicating appropriate precision and high accuracy of the SERS sensor. These results suggest that the SERS sensor of the present invention will be a promising method for clinical applications.

TABLE 5

| Parameters | Samples | | |
|---|---|---|---|
| | miR-21 | miR-222 | miR-200c |
| miRNA added (ng/mL) | 1.00 | 1.00 | 1.00 |
| miRNA detected (ng/mL)[a] | 0.95 | 1.01 | 0.98 |
| RSD (%) | 3.03 | 4.72 | 3.61 |
| Recovery (%) | 95.28 | 101.68 | 98.34 |

[a]Average values of five successive determinations.
RSD, relative standard deviations.

CONCLUSION

The SERS-based nanoplasmonic biosensor of the present invention can be used for label-free multiplex detection of miRNAs. In the present invention, three miRNAs (miR-10b, miR-21, and miR-373) involved in metastasis were used as targets. These target miRNAs are potential biomarkers of cancer. The SERS-based nanoplasmonic biosensor of the present invention was fabricated by the following procedure. First, a Si nanopillar mold was used to produce head-flocked gold nanopillars and cast slide glass was used for multiplex detection. A Si nanopillar structure was made via a maskless dry etching process (Jansen H., de Boer M., Legtenberg R., Elwenspoek M., and Micromech J., 1995. Microengin, 5, 115.) and gold was deposited on the silicon via an electron beam evaporation process (Diebold E. D., Mack N. H., Doom S. K., and E. Mazur, 2009. Langmuir 25, 1790). After sample treatment and drying, the ends of at least two of the gold nanopillars showed a tendency to converge towards a specific location. This tendency was named the "head-flocking" effect. Due to this phenomenon, nanometer-sized gaps were formed between the gold nanopillars, DNA probes, and the miRNA sample, resulting in the generation of hotspots. The gap formation enhanced plasmonic coupling effects.

In addition, when DNA probes complementary to the target miRNAs were designed to selectively multiplex detect the miRNAs, the DNA probes was divided into two different parts: a capture part (first DNA, capture DNA) directly conjugating with the head-flocked gold nanopillar structure and hybridizing with the target miRNA; and a detection part (second DNA, detection DNA) to confirm the signal transition during hybridization.

After completion of the procedure, fingerprint peaks for the target miRNAs were identified with high selectivity. Based on this, the nanoplasmonic biosensor of the present invention is capable of multiplex detection of miRNAs involved in signal transition, enabling both quantitative analysis of the miRNAs through concentration-dependent signal intensities and qualitative analysis of the miRNAs. In addition, the nanoplasmonic biosensor of the present invention can detect miRNAs in real time without pretreatment for miRNA purification or cDNA synthesis by qRT-PCR. Furthermore, the nanoplasmonic biosensor of the present invention can rapidly detect miR-10b, miR-21, and miR-373 in real time with low limits of detection (LOD) (5.46 fM (peak 1) and 3.53 fM (peak 2) for miR-10b, 3.16 fM (peak 1) and 2.08 fM (peak 2) for miR-21, and 1.73 fM (peak 1) and 2.16 fM (peak 2) for miR-373) and high efficiency.

In conclusion, the nanoplasmonic biosensor of the present invention is capable of label-free multiplex detection of miRNAs as disease markers in blood with high selectivity and sensitivity. Therefore, the nanoplasmonic biosensor of the present invention is expected to be effectively applicable to the diagnosis of miRNA-related diseases and clinical use.

INDUSTRIAL APPLICABILITY

The nanoplasmonic biosensor of the present invention is capable of label-free multiplex detection of miRNAs as disease markers in blood with high selectivity and sensitivity. Therefore, the nanoplasmonic biosensor of the present invention can be effectively used for the diagnosis of miRNA-related diseases and clinical applications.

---

The invention claimed is:

1. A nanoplasmonic biosensor comprising:
an elastic silicon substrate comprising a plurality of protrusions extended from and perpendicular to a surface of the elastic silicon substrate and spaced apart from one another on the surface of the elastic silicon substrate;
a plurality of gold nanopillars comprising the plurality of protrusions and a plurality of gold particles disposed on surfaces of the plurality of protrusions;
a capture part comprising a first single-stranded DNA or LNA comprising a first sequence complementary to a first portion of a sequence of a miRNA as a disease marker; and
a detection part comprising a second single-stranded DNA or LNA comprising a second sequence complementary to a second portion of the sequence of the miRNA,
wherein each of the plurality of gold nanopillars comprises a first end attached to the elastic silicon substrate and a second end, onto which at least one of the plurality of gold nanoparticles is disposed, disposed opposite to the first end,
wherein the capture part is conjugated with the second end of at least one of the plurality of gold nanopillars, and
wherein when the first portion of the sequence of the miRNA hybridizes with the capture part, at least two of the second ends of the plurality of gold nanopillars are converged toward a specific location.

2. The nanoplasmonic biosensor according to claim 1, wherein when the miRNA hybridizes with the capture part, a Raman signal is primarily amplified.

3. The nanoplasmonic biosensor according to claim 1, wherein when the second portion of the sequence of the miRNA hybridizes the detection part, a Raman signal is secondarily amplified.

4. The nanoplasmonic biosensor according to claim 1, wherein a thiol group at one end of the first single-stranded DNA or LNA is modified.

5. The nanoplasmonic biosensor according to claim 1, wherein the plurality of gold particles are further disposed on the surface of the substrate.

6. The nanoplasmonic biosensor according to claim 1, wherein the miRNA is selected from the group consisting of miR-10b, miR-21, miR-373, miR-222, and miR-200C.

* * * * *

SEQUENCE LISTING

```
<160> NUMBER OF SEQ ID NOS: 29

<210> SEQ ID NO 1
<211> LENGTH: 21
<212> TYPE: RNA
<213> ORGANISM: Artificial Sequence
<220> FEATURE:
<223> OTHER INFORMATION: miRNA

<400> SEQUENCE: 1
uacccuguag aaccgaauuu g                                        21

<210> SEQ ID NO 2
<211> LENGTH: 21
<212> TYPE: RNA
<213> ORGANISM: Artificial Sequence
<220> FEATURE:
<223> OTHER INFORMATION: miRNA

<400> SEQUENCE: 2
uagcuuauca gacugauguu g                                        21

<210> SEQ ID NO 3
<211> LENGTH: 21
<212> TYPE: RNA
```

```
<213> ORGANISM: Artificial Sequence
<220> FEATURE:
<223> OTHER INFORMATION: miRNA

<400> SEQUENCE: 3
cucaaaaugg gggcgcuuuc c                                              21

<210> SEQ ID NO 4
<211> LENGTH: 21
<212> TYPE: RNA
<213> ORGANISM: Artificial Sequence
<220> FEATURE:
<223> OTHER INFORMATION: LNA type

<400> SEQUENCE: 4
uacccuguag aaccgaauuu g                                              21

<210> SEQ ID NO 5
<211> LENGTH: 11
<212> TYPE: DNA
<213> ORGANISM: Artificial Sequence
<220> FEATURE:
<223> OTHER INFORMATION: DNA Capture probe

<400> SEQUENCE: 5
cacaaattcg g                                                         11

<210> SEQ ID NO 6
<211> LENGTH: 11
<212> TYPE: DNA
<213> ORGANISM: Artificial Sequence
<220> FEATURE:
<223> OTHER INFORMATION: DNA probe

<400> SEQUENCE: 6
tcaacatcag t                                                         11

<210> SEQ ID NO 7
<211> LENGTH: 11
<212> TYPE: DNA
<213> ORGANISM: Artificial Sequence
<220> FEATURE:
<223> OTHER INFORMATION: DNA probe

<400> SEQUENCE: 7
ggaaagcgcc c                                                         11

<210> SEQ ID NO 8
<211> LENGTH: 12
<212> TYPE: DNA
<213> ORGANISM: Artificial Sequence
<220> FEATURE:
<223> OTHER INFORMATION: LNA type

<400> SEQUENCE: 8
cacaaattcg gt                                                        12

<210> SEQ ID NO 9
<211> LENGTH: 12
<212> TYPE: DNA
<213> ORGANISM: Artificial Sequence
<220> FEATURE:
<223> OTHER INFORMATION: DNA type

<400> SEQUENCE: 9
ttctacaggg ta                                                        12
```

```
<210> SEQ ID NO 10
<211> LENGTH: 11
<212> TYPE: DNA
<213> ORGANISM: Artificial Sequence
<220> FEATURE:
<223> OTHER INFORMATION: DNA probe

<400> SEQUENCE: 10
ctgataagct a                                                           11

<210> SEQ ID NO 11
<211> LENGTH: 11
<212> TYPE: DNA
<213> ORGANISM: Artificial Sequence
<220> FEATURE:
<223> OTHER INFORMATION: DNA probe

<400> SEQUENCE: 11
ccattttgag t                                                           11

<210> SEQ ID NO 12
<211> LENGTH: 11
<212> TYPE: DNA
<213> ORGANISM: Artificial Sequence
<220> FEATURE:
<223> OTHER INFORMATION: LNA type

<400> SEQUENCE: 12
tctacagggt a                                                           11

<210> SEQ ID NO 13
<211> LENGTH: 22
<212> TYPE: RNA
<213> ORGANISM: Artificial Sequence
<220> FEATURE:
<223> OTHER INFORMATION: miRNA

<400> SEQUENCE: 13
uagcuuauca gacugauguu ga                                               22

<210> SEQ ID NO 14
<211> LENGTH: 22
<212> TYPE: RNA
<213> ORGANISM: Artificial Sequence
<220> FEATURE:
<223> OTHER INFORMATION: miRNA

<400> SEQUENCE: 14
uagcuuauca gacugaugua ga                                               22

<210> SEQ ID NO 15
<211> LENGTH: 22
<212> TYPE: RNA
<213> ORGANISM: Artificial Sequence
<220> FEATURE:
<223> OTHER INFORMATION: miRNA

<400> SEQUENCE: 15
uagcugauca gacugauguu ga                                               22

<210> SEQ ID NO 16
<211> LENGTH: 21
<212> TYPE: RNA
<213> ORGANISM: Artificial Sequence
<220> FEATURE:
```

<223> OTHER INFORMATION: miRNA

<400> SEQUENCE: 16
agcuacaucu ggcuacuggg u                                          21

<210> SEQ ID NO 17
<211> LENGTH: 21
<212> TYPE: RNA
<213> ORGANISM: Artificial Sequence
<220> FEATURE:
<223> OTHER INFORMATION: miRNA

<400> SEQUENCE: 17
agcuacaucu ggcuacugga u                                          21

<210> SEQ ID NO 18
<211> LENGTH: 21
<212> TYPE: RNA
<213> ORGANISM: Artificial Sequence
<220> FEATURE:
<223> OTHER INFORMATION: miRNA

<400> SEQUENCE: 18
agcuacaccu ggcuacuggg u                                          21

<210> SEQ ID NO 19
<211> LENGTH: 23
<212> TYPE: RNA
<213> ORGANISM: Artificial Sequence
<220> FEATURE:
<223> OTHER INFORMATION: miRNA

<400> SEQUENCE: 19
uaauacugcc ggguaaugau gga                                        23

<210> SEQ ID NO 20
<211> LENGTH: 23
<212> TYPE: RNA
<213> ORGANISM: Artificial Sequence
<220> FEATURE:
<223> OTHER INFORMATION: miRNA

<400> SEQUENCE: 20
uaauagugcc ggguaaugau gga                                        23

<210> SEQ ID NO 21
<211> LENGTH: 23
<212> TYPE: RNA
<213> ORGANISM: Artificial Sequence
<220> FEATURE:
<223> OTHER INFORMATION: miRNA

<400> SEQUENCE: 21
uaauacugcc ggguaaugau cga                                        23

<210> SEQ ID NO 22
<211> LENGTH: 22
<212> TYPE: RNA
<213> ORGANISM: Artificial Sequence
<220> FEATURE:
<223> OTHER INFORMATION: miRNA

<400> SEQUENCE: 22
uaacacuguc ugguaacgau gu                                         22

```
<210> SEQ ID NO 23
<211> LENGTH: 22
<212> TYPE: RNA
<213> ORGANISM: Artificial Sequence
<220> FEATURE:
<223> OTHER INFORMATION: miRNA

<400> SEQUENCE: 23
uaauacugcc ugguaaugau ga                                              22

<210> SEQ ID NO 24
<211> LENGTH: 12
<212> TYPE: DNA
<213> ORGANISM: Artificial Sequence
<220> FEATURE:
<223> OTHER INFORMATION: LNA Capture Probe

<400> SEQUENCE: 24
tcaacatcag tc                                                         12

<210> SEQ ID NO 25
<211> LENGTH: 11
<212> TYPE: DNA
<213> ORGANISM: Artificial Sequence
<220> FEATURE:
<223> OTHER INFORMATION: LNA Capture Probe

<400> SEQUENCE: 25
acccagtagc c                                                          11

<210> SEQ ID NO 26
<211> LENGTH: 12
<212> TYPE: DNA
<213> ORGANISM: Artificial Sequence
<220> FEATURE:
<223> OTHER INFORMATION: LNA Capture Probe

<400> SEQUENCE: 26
tccatcatta cc                                                         12

<210> SEQ ID NO 27
<211> LENGTH: 10
<212> TYPE: DNA
<213> ORGANISM: Artificial Sequence
<220> FEATURE:
<223> OTHER INFORMATION: LNA Detection Probe

<400> SEQUENCE: 27
tgataagcta                                                            10

<210> SEQ ID NO 28
<211> LENGTH: 10
<212> TYPE: DNA
<213> ORGANISM: Artificial Sequence
<220> FEATURE:
<223> OTHER INFORMATION: LNA Detection Probe

<400> SEQUENCE: 28
agatgtagct                                                            10

<210> SEQ ID NO 29
<211> LENGTH: 11
<212> TYPE: DNA
<213> ORGANISM: Artificial Sequence
<220> FEATURE:
<223> OTHER INFORMATION: LNA Detection Probe
```

```
<400> SEQUENCE: 29
cggcagtatt a                                                              11
```